US009737575B2

(12) United States Patent
Crane et al.

(10) Patent No.: US 9,737,575 B2
(45) Date of Patent: Aug. 22, 2017

(54) USE OF LACTIC ACID BACTERIA TO TREAT OR PREVENT ECZEMA

(75) Inventors: Julian Crane, Wellington (NZ); Angela Marie Rowan, Palmerston North (NZ); Kristin Lee Wickens, Wellington (NZ); Gerald William Tannock, Dunedin (NZ); Thorsten Villiers Stanley, Wellington (NZ); Penelope Frances Fitzharris, Auckland (NZ); Edwin Arthur Mitchell, Auckland (NZ); Peter Nigel Black, Auckland (NZ); Bernadette Salmon, legal representative, Auckland (NZ)

(73) Assignee: UNIVERSITY OF OTAGO, Dunedin (NZ)

(*) Notice: Subject to any disclaimer, the term of this patent is extended or adjusted under 35 U.S.C. 154(b) by 403 days.

(21) Appl. No.: 13/130,522

(22) PCT Filed: Nov. 28, 2008

(86) PCT No.: PCT/NZ2008/000321
§ 371 (c)(1),
(2), (4) Date: Nov. 8, 2011

(87) PCT Pub. No.: WO2010/064930
PCT Pub. Date: Jun. 10, 2010

(65) Prior Publication Data
US 2012/0045422 A1 Feb. 23, 2012

(51) Int. Cl.
| A61K 35/74 | (2015.01) |
| A61K 35/747 | (2015.01) |
| A61K 31/702 | (2006.01) |
| A61K 31/733 | (2006.01) |
| A61K 45/06 | (2006.01) |
| A23L 33/00 | (2016.01) |
| A23L 33/135 | (2016.01) |

(52) U.S. Cl.
CPC .......... *A61K 35/747* (2013.01); *A23L 33/135* (2016.08); *A23L 33/40* (2016.08); *A61K 31/702* (2013.01); *A61K 31/733* (2013.01); *A61K 45/06* (2013.01); *A23V 2002/00* (2013.01); *A23Y 2220/73* (2013.01); *Y10S 514/861* (2013.01)

(58) Field of Classification Search
None
See application file for complete search history.

(56) References Cited

FOREIGN PATENT DOCUMENTS

| WO | WO 99/10476 | * 3/1999 |
| WO | WO 03/082921 | 10/2003 |
| WO | WO 2007/043900 | 4/2007 |
| WO | WO 2007/098564 | 9/2007 |
| WO | WO 2007/101675 | 9/2007 |
| WO | WO 2007/108763 | 9/2007 |
| WO | WO 2007/123488 | 11/2007 |
| WO | WO 2008/055296 | 5/2008 |
| WO | WO 2011/099875 | 8/2011 |

OTHER PUBLICATIONS

Wickens et al., Journal of Allergy and Clinical Immunology, vol. 122, No. 4, p. 788-794, 2008, published online Sep. 2, 2008.*
Vandenplas (British Journal of Nutrition, vol. 87, Supplement 2, p. S293-S296, 2002).*
Kalliomaki et al. (The Lancet, vol. 361, p. 1869-1871, 2003).*
Vendt et al. (Journal of Human Nutrition and Dietetics, vol. 19, No. 1, p. 51-58, 2006).*
International Search Report and Written Opinion of the International Searching Authority dated May 28, 2009, for International Patent Application No. PCT/NZ2008/000321.
Passeron et al., Prebiotics and Synbiotics: Two Promising Approaches for the Treatment of Atopic Dermatitis in Children Above 2 Years, Allergy, 2006, vol. 61, pp. 431-437.
Rosenfeldt et al., Effect of Probiotic Lactobacillus Strains in Children with Atopic Dermatitis, Journal of Allergy and Clinical Immunology, 2003, vol. 111, Issue 2, pp. 389-395.
Wickens et al., A Differential Effect of 2 Probiotics in the Prevention of Eczema and Atopy: A Double-Blind, Randomized, Placebo-Controlled Trial, Journal of Allergy and Clinical Immunology, 2008, vol. 122, Issue 4, pp. 788-794.
Leyer et al., "24-2, Screening procedure for the selection of probiotics with immunomodulation potential", available at: http://ift.confex.com/ift/2004/techprogram/paper_21317.htm, 2004, 1 page.
Mercenier et al., "Screening and Construction of Probiotic Strains with Enhanced Protective Properties against Intestinal Disorders", Microbial Ecology in Health and Disease, 2004; vol. 16, pp. 86-95.
Ahrne et al., "The normal *Lactobacillus* flora of healthy human rectal and oral mucosa", J Appl Microbiol., 1998; vol. 85, pp. 88-94.
Ascia Skin Prick Testing Working Party, "Skin prick testing for the diagnosis of allergic disease: a manual for practitioners", 2006, Available at: http://www.allergy.org.au/images/stories/pospapers/ASCIA_SPT_Manual_Sep_06.pdf.
Blumer et al., "Perinatal maternal application of *Lactobacillus rhamnosus* GG suppresses allergic airway inflammation in mouse offspring", Clin Exp Allergy, 2007, vol. 37, pp. 348-357.
Boehm et al., "Structural and Functional Aspects of Prebiotics Used in Infant Nutrition", J. Nutr., 2008,vol. 138, No. 9, pp. 1818S-1828S.
Collett et al., "Lactobacillus rhamnosus HN001, whole genome shotgun sequencing project", Genbank accession No. NZ_ABWJ00000000, Available at: http://www.ncbi.nlm.nih.gov/nuccore/nz_abwj00000000.
Cummings et al., PASSCLAIM Process for the Assessment of Scientific Support for Claims on Foods, Phase Two: Moving Forward, Eur J. Nutr., 2004, Suppl 2, vol. 43, pp. II/1-II/2.
Epton et al., "The New Zealand Asthma and Allergy Cohort Study (NZA2CS): assembly, demographics and investigations", BMC Public Health, 2007, vol. 7, No. 26, pp. 1-9.

(Continued)

*Primary Examiner* — Thane Underdahl
(74) *Attorney, Agent, or Firm* — Knobbe, Martens, Olson & Bear LLP

(57) ABSTRACT

Use of *Lactobacillus rhamnosus* HN001 or derivatives thereof to treat or prevent eczema.

15 Claims, 3 Drawing Sheets

(56) References Cited

OTHER PUBLICATIONS

Janer et al., "Enzymatic ability of *Bifidobacterium animalis* subsp. *lactis* to hydrolyze milk proteins: identification and characterization to endopeptidase O", Appl Environ Microbiol, 2005, vol. 71, No. 12, pp. 8460-8465.
Kalliomaki et al., "Probiotics during the first 7 years of life: a cumulative risk reduction of eczema in a randomized, placebo-controlled trial", J Allergy Clin Immunol, 2007, vol. 119, pp. 1019-1021.
Kim et al., "Biological and genetic classification of canine intestinal lactic acid bacteria and bifidobacteria", Microbiol Immunol., 2007, vol. 51, No. 10, pp. 919-928.
Kukkonen et al., "Probiotics and prebiotics galacto-oligosaccharides in the prevention of allergic disease: a randomized, double-blind, placebo-controlled trial", J Allergy Clin Immunol., 2007, vol. 119, pp. 192-198.
Mah et al., "Effect of milk formula containing probiotics on the fecal microbiota of Asian infants at risk of atopic diseases" Pediatr Res., 2007, vol. 62, No. 6, pp. 674-679.
Niers et al., "Identification of strong interleukin-10 inducing lactic acid bacteria which down-regulate T helper type 2 cytokines" Clin Exp Allergy, 2005, vol. 35, pp. 1481-1489.
Prescott et al., "Probiotics for the prevention or treatment of allergic diseases", J Allergy Clin Immunol., 2007, 120, pp. 255-262.
Prescott et al., "Supplementation with *Lactobacillus rhamnosus* or *Bifidobacterium lactis* probiotics in pregnancy increases cord blood IFN-gamma and breast milk TGF-beta and IgA detection", Clin Exp Allergy, 2008, vol. 38, pp. 1606-1614.
Requena et al., "Identification, detection, and enumeration of human *Bifidobacterium* species by PCR targeting the transaldolase gene", Appl Environ Microbiol, 2002, vol. 68, pp. 2420-2427.
Stalder et al., "Severity Scoring of Atopic Dermatitis: the SCORAD Index", Dermatology, 1993, vol. 186, pp. 23-31.
Strachan, D., "Family size, infection and atopy: the first decade of the "hygiene hypothesis", Thorax, 2000, vol. 55 (suppl 1), pp. S2-10.
Tannock et al., "Analysis of the fecal microflora of human subjects consuming a probiotic containing *Lactobacillus rhamnosus* DR20", Appl Environ Microbiol., 2000, vol. 66, pp. 2578-2588.
Taylor et al., "Probiotic supplementation for the first 6 months of life fails to reduce the risk of atopic dermatitis and increases the risk of allergen sensitization in high-risk children: a randomized controlled trial", J Allergy Clin Immunol., 2007, vol. 119, No. 1, pp. 184-191.
Vaarala G., "Immunological effects of probiotics with special reference to lactobacilli", Clin Exp Allergy, 2003, vol. 33, pp. 1634-1640.
Walter et al., "Detection of *Lactobacillus, Pediococcus, Leuconostic* and *Weisellall* species in human feces by using group-specific PCR primers and denaturing gradient gel electrophoresis", Appl Environ Microbiol., 2001, vol. 67, No. 6, pp. 2578-2585.
Wickens et al., "A Differential Effect of Two Probiotics in the Prevention of Eczema and Atopy", poster presented at the World Allergy Congress Dec. 2-6, 2007.
Wickens et al., "A Differential Effect of Two Probiotics in the Prevention of Eczema and Atopy", poster presented at the International Probiotics Association Apr. 11-12, 2008.
Williams et al., "So How Do I Define Atopic Eczema? A Practical Manual for Researchers Wanting to Define Atopic Eczema", 1996, available at: http://www.nottingham.ac.uk/dermatology/eczema/contents/html.
Williams et al., "The UK Working Party's Diagnostic Criteria for Atopic Dermatitis", Br J Dermatol., 1994, vol. 131, pp. 383-396.
Abrahamsson et al., Probiotics in prevention of IgE-associated eczema: A double-blind, randomized, placebo-controlled trial, J Allergy Clin Immunol 2007; 119:1174-80.
Boyle et al., "Lactobacillus GG treatment during pregnancy for the prevention of eczema: a randomized controlled trial", Allergy 2011; 66:509-16.
Kalliomäki et al., "Probiotics in primary prevention of atopic disease: A randomised placebo-controlled trial", The Lancet 2001; 119:1019-21.
Prasad et al., "Selection and Characterisation of Lactobacillus and Bifidobacterium Strains for Use as Probiotics", International Diary Journal 1998; 8: 993-1002.
Soh et al., "Probiotic supplementation in the first 6 months of life in at risk Asian infants—effects on eczema and atopic sensitization at the age of 1 year", S. E., Clinical and Experimental Allergy 2009; 39:571-8.
Wickens et al., "A protective effect of Lactobacillus rhamnosus HN001 against eczema in the first two years of life persists to age 4 years", Clinical & Experimental Allergy, Blackwell Publishing Ltd., 2012, 42, pp. 1071-1079.
Wickens et al. "Early supplementation with Lactobacillus rhamnosus HN001 reduces eczema prevalence to 6 years: does it also reduce atopic sensitization?", Clinical & Experimental Allergey, Blackwell Publishing Ltd., 2013, 43, pp. 1048-1057.
Zhou, "Safety Studies on Probiotic Strains Lactobacillus rhamnous HN001, Lactobacillus acidophilus HN017, and Bifidobacterium lactis HN019", Ph.D, thesis, Massey University, New Zealand, pp. 1-225.
"Severity Scoring Atopic Dermatitis: the SCORAD index. Consensus Report of the European Task Force on Atopic Dermatitis", Dermatology, S. Karger AG, 1993, 186(1), pp. 23-31.

\* cited by examiner

USE OF LACTIC ACID BACTERIA TO TREAT OR PREVENT ECZEMA

REFERENCE TO RELATED APPLICATIONS

This application is the U.S. National Phase of International Application PCT/NZ2008/000321, filed Nov. 28, 2008, which is hereby incorporated by reference in its entirety.

TECHNICAL FIELD

This invention relates to the use of probiotic bacteria and in particular the use of a strain of lactic acid bacteria to treat or prevent eczema. Methods for using the bacteria and compositions comprising the bacteria are also provided.

BACKGROUND

In 1989, Strachan (Strachan D. Family size, infection and atopy: the first decade of the "hygiene hypothesis". Thorax 2000; 55(suppl 1):S2-10) suggested that decreased exposure to infections could explain the increasing prevalence of allergic disease in Western countries. This has become known as the hygiene hypothesis.

Since then, numerous investigations have attempted to discern a role for organisms such as lactobacilli in immunological maturation (Vaarala G. Immunological effects of probiotics with special reference to lactobacilli. Clin Exp Allergy 2003; 33:1634-40; Blumer N, Sel S, Virna S, Patrascan C, Zimmermann S, Herz U, et al. Perinatal maternal application of *Lactobacillus rhamnosus* GG suppresses allergic airway inflammation in mouse offspring. Clin Exp Allergy 2007; 37:348-57) and the effect of probiotics on the development of allergic disease.

The efficacy of prenatal or neonatal administration of *Lactobacillus rhamnosus* GG, *Lactobacillus acidophilus* LAVR1-A1, or *Lactobacillus reuteri* ATCC 55730 on the development of allergic disease is conflicting, with various studies reporting divergent findings. One study reported that administration of *Lactobacillus rhamnosus* GG halved the frequency of eczema at 2, 4, and 7 years, but had no effect on atopic sensitization (see Kalliomaki M, Salminen S, Poussa T, Isolauri E. Probiotics during the first 7 years of life: a cumulative risk reduction of eczema in a randomized, placebo-controlled trial. J Allergy Clin Immunol 2007; 119: 1019-21). Other studies have found no effect of *Lactobacillus acidophilus* or *L. rhamnosus* GG on atopic dermatitis, with one of these studies finding that *L. acidophilus* supplementation actually increased the risk of atopic sensitization (Taylor A, Dunstan J, Prescott S. Probiotic supplementation for the first 6 months of life fails to reduce the risk of atopic dermatitis and increases the risk of allergen sensitization in high-risk children: a randomized controlled trial. J Allergy Clin Immunol 2007; 119:184-91). It has been suggested that the different organisms used and whether there was a prenatal intervention may have influenced the divergent findings.

Furthermore, while a range of treatments for allergic diseases such as eczema are currently available, those suitable for use during pregnancy are limited, and frequently of limited efficacy.

There remains a need for methods and compositions useful to treat or prevent allergic disease, in particular eczema, and particularly methods and compositions utilizing or comprising other lactobacilli.

It is an object of this invention to go some way towards achieving one or ore of these desiderata or at least to offer the public a useful choice.

SUMMARY OF THE INVENTION

In a first aspect the invention provides a method of treating or preventing eczema in a subject, the method comprising administration of *Lactobacillus rhamnosus* HN001, AGAL deposit number NM97/09514 dated 18 Aug. 1997 to a subject in need thereof.

In one embodiment, the *L. rhamnosus* HN001 is administered in the form of a composition with a physiologically acceptable diluent, adjuvant, carrier or excipient.

In one embodiment, said physiologically acceptable diluent, adjuvant, carrier or excipient is a food. In one embodiment, the food is cultured milk, yoghurt, cheese, milk drink or milk powder.

Alternatively the composition is a pharmaceutical composition and said excipient or diluent is pharmaceutically acceptable diluent, adjuvant, carrier or excipient.

In embodiments where the subject is a foetal subject, the method comprises administering the *L. rhamnosus* HN001 or a composition comprising *L. rhamnosus* HN001 to the foetal subject's mother. It will be appreciated that in such embodiments, the administration to the subject may be considered indirect administration. In one embodiment, the composition is a maternal formula or a maternal supplement. In such embodiments, the method preferably relates to prevention of eczema.

In certain embodiments where the subject is a neonatal, an infant, or a child subject, the method comprises administering a composition comprising *L. rhamnosus* HN001 to the subject. Again, it will be appreciated that in such embodiments, the administration to the subject may be considered direct administration.

In other embodiments, such as where the subject is a breastfeeding neonatal, infant, or child subject, the method comprises administering the *L. rhamnosus* HN001 or a composition comprising *L. rhamnosus* HN001 to the subject's mother. It will be appreciated that in such embodiments, the administration to the subject may be considered indirect administration.

The composition may be an infant formula, follow-on formula, growing-up formula or dietetic product, including hypoallergenic embodiments of such compositions.

In preferred embodiments where the subject is a juvenile or an adult subject, the method comprises administering a composition comprising *L. rhamnosus* HN001 to the subject. Preferably, the composition is a supplement, formula, dietetic product or food.

In certain embodiments, the *L. rhamnosus* HN001 is in a reproductively viable form, preferably in a reproductively viable form and amount. In other embodiments, the *L. rhamnosus* HN001 is killed, lysed, fractionated or attenuated.

In one embodiment, the eczema is atopic eczema. In various embodiments, the eczema is selected from the group comprising atopic eczema (also known as infantile eczema, flexural eczema or atopic dermatitis), xerotic eczema (also known as asteatotic eczema), seborrhoeic dermatitis, dyshidrosis, discoid eczema, venous eczema, Duhring's disease, or neurodermatitis.

The invention further provides *L. rhamnosus* HN001 for treating or preventing eczema and *L. rhamnosus* HN001 in the manufacture of a composition for treating or preventing eczema. The composition may be a composition such as those as described below including, for example, a food or medicament.

It will be appreciated that the invention also contemplates the use of *L. rhamnosus* HN001 in the manufacture of a composition of the invention, for example a composition for treating or preventing eczema in a subject.

In one embodiment the composition is suitable for oral administration. In other embodiments, the composition is suitable for parenteral administration. In embodiments relating to preventing eczema in a foetal subject, the composition is suitable for oral administration to a pregnant mother during gestation.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

DETAILED DESCRIPTION OF THE INVENTION

Figure 1:
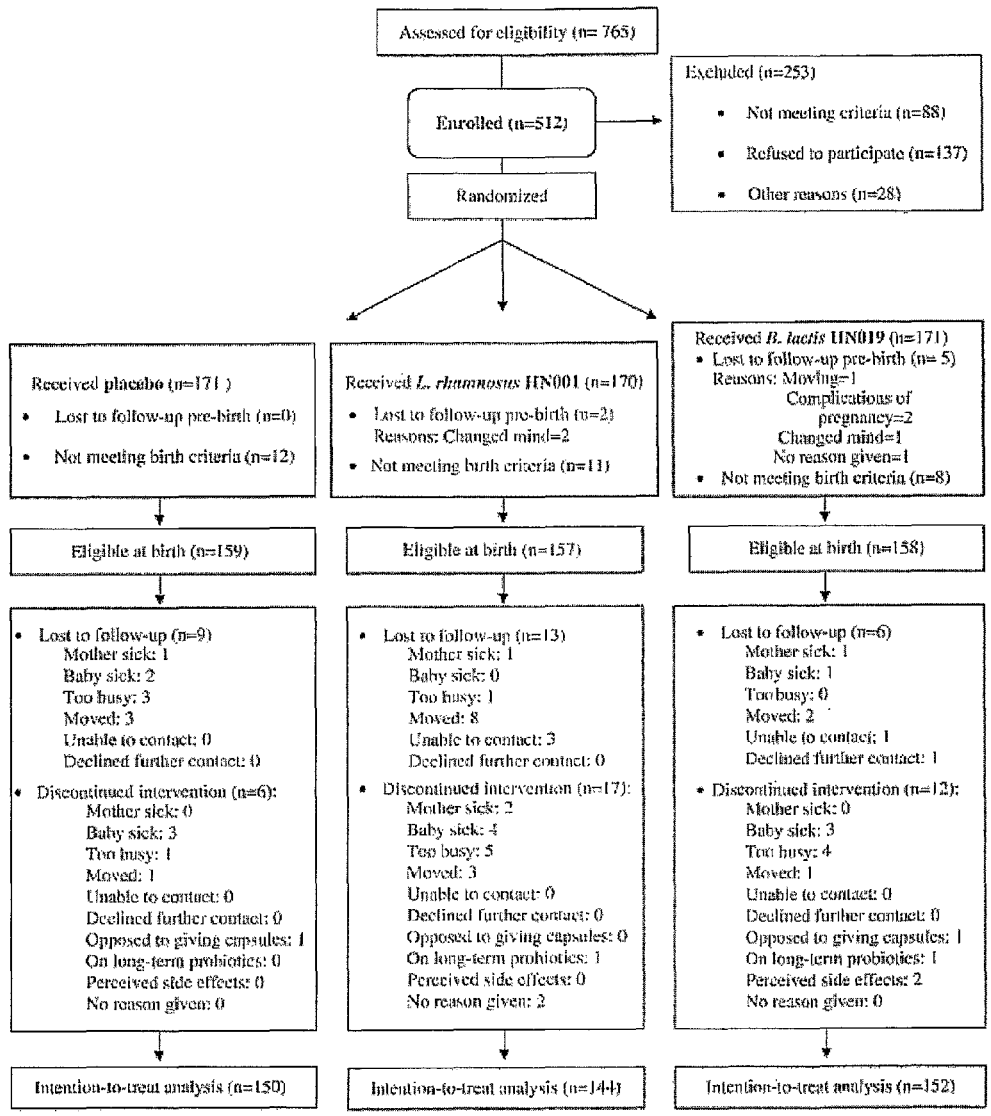
FIG. 1 is a diagram showing the flow of participants in the placebo, *L. rhamnosus* HN001, and *B. animalis* subsp *lactis* HN019 groups in the trial described in Example 1 herein.

The present invention recognises for the first time the beneficial effects of administration of the lactic acid bacteria *L. rhamnosus* HN001 on the incidence and severity of eczema.

Accordingly, in a first aspect the invention provides a method of treating or preventing eczema in a subject, the method comprising administration of *Lactobacillus rhamnosus* HN001, AGAL deposit number NM97/09514 dated 18 Aug. 1997 or a derivative thereof to a subject in need thereof.

While various routes and methods of administration are contemplated, oral administration of *L. rhamnosus* HN001, such as in a composition suitable for oral administration, is currently preferred. It will of course be appreciated that other routes and methods of administration may be utilised or preferred in certain circumstances. For example, a parenteral route may be utilised with a composition comprising killed or attenuated *L. rhamnosus* HN001 or a derivative thereof.

The term "oral administration" includes oral, buccal, enteral and intra-gastric administration.

The term "parenteral administration" includes but is not limited to topical (including administration to any dermal, epidermal or mucosal surface), subcutaneous, intravenous, intraperitoneal, and intramuscular administration.

A "subject" is an animal, preferably a mammal, more preferably a mammalian companion animal or human. Preferred companion animals include cats, dogs and horses. In one embodiment the human is an adult, a child, an infant, a neonate, or a foetus. In various embodiments, the human child, infant or neonate is a breastfeeding child, infant or neonate.

The term "treat" and its derivatives should be interpreted in their broadest possible context. The term should not be taken to imply that a subject is treated until total recovery. Accordingly, "treat" broadly includes amelioration and/or prevention of the onset of the symptoms or severity of a particular condition.

It will be appreciated that treatment includes prophylactic treatment, such as for example, the prophylactic treatment of a foetal subject by indirect administration of a composition of the invention by administering the composition to the foetal subject's mother.

In another example, the prophylactic treatment is of a breastfeeding neonatal, infant or child subject by indirect administration of a composition of the invention by administering the composition to the neonatal, infant, or child subject's mother.

It will be further appreciated that treatment includes therapeutic treatment, such as for example, treatment of eczema or one or more symptoms of eczema, including for example the treatment of an neonatal, infant or child subject by indirect administration of a composition of the invention by administering the composition to the subject's mother.

Accordingly, the invention provides a method of preventing eczema in a foetal subject, the method comprising administration of *L. rhamnosus* HN001 or a composition comprising *L. rhamnosus* HN001 to the subject's mother. Particularly contemplated is a method of preventing eczema in a foetal subject.

The invention further provides a method of treating or preventing eczema in a breastfeeding neonatal, infant, or child subject, the method comprises administering *L. rhamnosus* HN001 or a composition comprising *L. rhamnosus* HN001 to the subject's mother. Particularly contemplated is a method of preventing eczema in a neonatal, infant or child subject.

Also provided is a method of treating or preventing eczema in a neonatal, infant, or child subject, the method comprises administering *L. rhamnosus* HN001 or a composition comprising *L. rhamnosus* HN001 to the subject. Particularly contemplated is a method of preventing eczema in a neonatal, infant or child subject.

A method of treating eczema in an infant or child subject comprising administering a composition consisting of or consisting essentially of *L. rhamnosus* HN001 is also contemplated.

In certain embodiments, the infant or child is one or more years of age.

In certain embodiments, the infant or child is a food-sensitised infant or child.

In certain embodiments, the infant or child is considered to be at risk of eczema due to the presence of allergy in one or both of its biological parents.

1 *Lactobacillus rhamnosus* HN001

As described in the applicant's PCT International application PCT/NZ98/00122 (published as WO 99/10476 and incorporated herein in its entirety), a freeze-dried culture of *Lactobacillus rhamnosus* HN001 was deposited at the Australian Government Analytical Laboratories (AGAL), The New South Wales Regional Laboratory, 1 Suakin Street, Pymble, NSW 2073, Australia, on 18 Aug. 1997 and was accorded deposit number NM97/09514. This Budapest Treaty-recognised depository is now no longer referred to as AGAL, but rather is referred to as the National Measurement Institute of Australia (NMIA). The genome sequence of *L. rhamnosus* HN001 is available at Genebank under accession number: NZ_ABWJ00000000.

1.1 Morphological Properties

The morphological properties of *L. rhamnosus* HN001 are described below.

Short to medium rods with square ends in chains, generally 0.7×1.1×2.0–4.0 μm, when grown in MRS broth.

Gram positive, non-mobile, non-spore forming, catalase negative facultative anaerobic rods with optimum growth temperature of 37±1° C. and optimum pH of 6.0-6.5. These are facultatively heterofermentative bacteria and no gas is produced from glucose.

1.2 Fermentative Properties

An API 50 CH sugar fermentation kit was used to determine the carbohydrate fermentation pattern of *L. rhamnosus* HN001, yielding a score of 5757177 (based on scores of 22 prominent sugars—see PCT/NZ98/00122).

1.3 Further Characterisation

*L. rhamnosus* strain HN001 may be further characterised by the functional attributes disclosed in PCT/NZ98/00122, including its ability to adhere to human intestinal epithelial cells, and by the improvements in phagocyte function, in antibody responses, in natural killer cell activity, and in lymphocyte proliferation elicited by dietary intake or in in vitro model systems. It will be appreciated that there are a wide variety of methods known and available to the skilled artisan that can be used to confirm the identity of *L. rhamnosus* HN001, wherein exemplary methods include DNA fingerprinting, genomic analysis, sequencing, and related genomic and proteomic techniques.

As described herein, certain embodiments of the present invention utilise live *L. rhamnosus* HN001. In other embodiments, a *L. rhamnosus* HN001 derivative is utilised.

As used herein, the term "derivative" and grammatical equivalents thereof when used with reference to bacteria (including use with reference to a specific strain of bacteria such as *L. rhamnosus* HN001) contemplates mutants and homologues of or derived from the bacteria, killed or attenuated bacteria such as but not limited to heat-killed, lysed, fractionated, pressure-killed, irradiated, and UV- or light-treated bacteria, and material derived from the bacteria including but not limited to bacterial cell wall compositions, bacterial cell lysates, lyophilised bacteria, probiotic factors from the bacteria, and the like, wherein the derivative retains probiotic activity. Methods to produce such derivatives, such as but not limited to one or more mutants of *L. rhamnosus* HN001 or one or more probiotic factors, and particularly derivatives suitable for administration to a subject (for example, in a composition) are well-known in the art.

It will be appreciated that methods suitable for identifying *L. rhamnosus* HN001, such as those described above, are similarly suitable for identifying derivatives of *L. rhamnosus* HN001, including for example mutants or homologues of *L. rhamnosus* HN001, or for example probiotic factors from *L. rhamnosus* HN001.

The term "probiotic factor" refers to a bacterial molecule responsible for mediating probiotic activity, including but not limited to bacterial DNA motifs, surface proteins, small organic acids, polysaccharides, or cell wall components such as lipoteichoic acids and peptidoglycan, or a mixture of any two or more thereof. While, as noted above, these molecules have not been clearly identified, and without wishing to be bound by any theory, such molecules will be present if a probiotic organism is present.

The term "probiotic activity" refers to the ability of certain microorganisms to stimulate the immune system. Measuring the type and level of activity of a probiotic microorganism is known to those skilled in the art; see, for example, Mercenier et al. (2004), Leyer et al. (2004), or Cummings et al. (2004). For example, probiotic activity may be assessed by a PBMC cytokine secretion assay.

Reference to retaining probiotic activity is intended to mean that a derivative of a probiotic microorganism, such as a mutant or homologue of a probiotic microorganism or an attenuated or killed probiotic microorganism still has useful probiotic activity, or that a composition comprising a probiotic microorganism or a derivative thereof is capable of supporting the maintenance of useful probiotic activity. While the bacterial molecules responsible for mediating probiotic activity have not been clearly identified, molecules that have been proposed as possible candidates include bacterial DNA motifs, surface proteins, small organic acids, polysaccharides, and cell wall components such as lipoteichoic acids and peptidoglycan. It has been postulated that these interact with components of the host immune system to give an immuno-modulatory effect. Preferably, the retained activity is at least about 35, 40, 45, 50, 55, 60, 65, 70, 75, 80, 85, 90, 95, 99 or 100% of the activity of an untreated (i.e., live or non-attenuated) control, and useful ranges may be selected between any of these values (for example, from about 35 to about 100%, from about 50 to about 100%, from about 60 to about 100%, from about 70 to about 100%, from about 80 to about 100%, and from about 90 to about 100%).

Using conventional solid substrate and liquid fermentation technologies well known in the art, *L. rhamnosus* HN001 can be grown in sufficient amounts to allow use as contemplated herein. For example, *L. rhamnosus* HN001 can be produced in bulk for formulation using nutrient film or submerged culture growing techniques, for example under conditions as described in WO99/10476. Briefly, growth is effected under aerobic conditions at any temperature satisfactory for growth of the organism. For example, for *L. rhamnosus* HN001 a temperature range of from 30 to 40° C., preferably 37° C., is preferred. The pH of the growth medium is slightly acidic, preferably about 6.0 to 6.5. Incubation time is sufficient for the isolate to reach a stationary growth phase.

*L. rhamnosus* HN001 cells may be harvested by methods well known in the art, for example, by conventional filtering or sedimentary methodologies (eg. centrifugation) or harvested dry using a cyclone system. *L. rhamnosus* HN001 cells can be used immediately or stored, preferably freeze-dried or chilled at −20° to 6° C., preferably −4° C., for as long as required using standard techniques.

2 Compositions

A composition useful herein may be formulated as a food, drink, food additive, drink additive, dietary supplement, nutritional product, medical food, enteral or parenteral feeding product, meal replacement, cosmeceutical, nutraceutical, or pharmaceutical. Appropriate formulations may be prepared by an art skilled worker with regard to that skill and the teaching of this specification.

In one embodiment, compositions useful herein include any edible consumer product which is able to carry bacteria or a bacterial derivative. Examples of suitable edible consumer products include powders, liquids, confectionary products including chocolate, gels, ice creams, reconstituted fruit products, snack bars, food bars, muesli bars, spreads, sauces, dips, dairy products including yoghurts and cheeses, drinks including dairy and non-dairy based drinks (such as milk drinks and yogurt drinks), milk powders, sports supplements including dairy and non-dairy based sports supplements, food additives such as protein sprinkles, dietary supplement products including daily supplement tablets, weaning foods and yoghurts, and formulas such as infant formula, follow-on formula, or growing-up formula, in powder or liquid form, including hypoallergenic embodiments of such compositions. Within this embodiment, a preferred composition useful herein may be an infant formula, follow-on formula or growing-up formula, in powder or liquid form. Suitable nutraceutical compositions useful herein may be provided in similar forms.

Examples of formulas such as infant formula, follow-on formula, or growing-up formula, in powder or liquid form, include the following. It should be understood that the following formulations are indicative only and variations may be made according to known principles for formulating such products. For example, non-dairy sources of protein may be supplemented for the dairy proteins listed. Equally, hypoallergenic embodiments of these products may be provided where the protein source is fully or partially hydrolysed. Such hydrolysates are known in the art. One example of an infant formula, follow-on formula or growing-up formula useful herein comprises (w/w)

30-60% lactose
15-35% vegetable oils
0-40% skim milk powder
0-40% whey protein, such as a WPC or WPI, preferably an 80% WPC (WPC80)
0.001-50% of *L. rhamnosus* HN001.

Another example of an infant formula, follow-on formula or growing-up formula useful herein comprises (w/w)

40-60% lactose
20-30% vegetable oils
10-15% skim milk powder
6-8% whey protein, preferably WPC80
0.001-10% of *L. rhamnosus* HN001.

Another example of an infant formula, follow-on formula or growing-up formula useful herein comprises (w/w)

40-60% lactose
20-30% vegetable oils
10-15% skim milk powder
6-8% whey protein, preferably WPC80
0.001-5% of *L. rhamnosus* HN001.

Another example of an infant formula, follow-on formula or growing-up formula useful herein comprises (w/w)

40-60% lactose
20-30% vegetable oils
10-15% skim milk powder
6-8% whey protein, preferably WPC80
0.001-2% of *L. rhamnosus* HN001.

Any of these infant formulas may also comprise 0.1 to 4% w/w, preferably 2 to 4% w/w of one or more of a vitamin premix, a mineral premix, lecithin, one or more antioxidants, one or more stabilisers, or one or more nucleotides, or a combination of any two or more thereof. In some embodiments, these infant formulas may be formulated to provide between 2700 and 3000 kJ/L.

Examples of edible consumer products of the invention, such as dairy based drinks (such as milk drinks and yogurt drinks) will typically comprise and may consist of a protein source (such as a dairy protein source), a lipid source, a carbohydrate source, in addition to the *L. rhamnosus* HN001 or derivative thereof. Flavourants, colourants, and other additives, carriers or excipients as are well known to those skilled in the art may also be included.

A further example of an edible consumer product amenable to use in the present invention is the Unistraw™ delivery system (Unistraw International Limited, Australia) as described in PCT international application PCT/AU2007/000265 (published as WO 2007/098564) and PCT international application PCT/AU2007/001698 (published as WO 2008/055296), each incorporated herein in its entirety. It will be appreciated by those skilled in the art that *L. rhamnosus* HN001 and derivatives thereof, optionally together with one or more additional probiotic factor or probiotic agent, may be coated onto a substrate (for example, a water soluble bead) for use in such delivery systems.

In alternative embodiments, the compositions useful herein may be formulated to allow for administration to a subject by any chosen route, including but not limited to oral or parenteral (including topical, subcutaneous, intramuscular and intravenous) administration.

For example, a nutraceutical composition for use according to the invention can be a dietary supplement (e.g., a capsule, a mini-bag, or a tablet) or a food product (e.g., milk, juice, a soft drink, a herbal tea-bag, or confectionary). The composition can also include other nutrients, such as a protein, a carbohydrate, vitamins, minerals, or amino acids. The composition can be in a form suitable for oral use, such as a tablet, a hard or soft capsule, an aqueous or oil suspension, or a syrup; or in a form suitable for parenteral use, such as an aqueous propylene glycol solution, or a buffered aqueous solution. The amount of the active ingredient in the nutraceutical composition depends to a large extent on a subject's specific need. The amount also varies, as recognized by those skilled in the art, dependent on administration route, and possible co-usage of other probiotic factors or probiotic agents.

It will be appreciated that in certain embodiments, the compositions of the invention may be formulated so as to have a desired calorific content, for example so as to deliver a desired amount of energy or a desired percentage of daily recommended energy intake. For example, an edible consumer product may be formulated to provide from about 200 to about 2000 kJ per serve, or from about 500 kJ to about 2000 kJ per serve, or from about 1000 to about 2000 kJ per serve.

Thus, a pharmaceutical composition useful according to the invention may be formulated with an appropriate pharmaceutically acceptable carrier (including excipients, diluents, auxiliaries, and combinations thereof) selected with regard to the intended route of administration and standard pharmaceutical practice. For example, a composition useful according to the invention can be administered orally as a powder, liquid, tablet or capsule, or topically as an ointment, cream or lotion. Suitable formulations may contain additional agents as required, including emulsifying, antioxidant, flavouring or colouring agents, and may be adapted for immediate-, delayed-, modified-, sustained-, pulsed- or controlled-release.

The term "pharmaceutically acceptable carrier" is intended to refer to a carrier including but not limited to an excipient, diluent or auxiliary, pharmaceutically acceptable carrier includes a solvent, a dispersion medium, a coating, an antibacterial and antifungal agent, and an isotonic and absorption delaying agent or combination thereof, that can be administered to a subject as a component of a composition described herein that does not reduce the activity of the composition and is not toxic when administered in doses sufficient to deliver an effective amount of a compound or composition useful herein. The formulations can be administered orally, nasally or parenterally (including topically, intramuscularly, intraperitoneally, subcutaneously and intravenously).

In certain embodiments, a composition of the invention (such as, for example, a nutraceutical or pharmaceutical composition of the invention, may be provided as a capsule. Capsules can contain any standard pharmaceutically acceptable materials such as gelatin or cellulose. Tablets can be formulated in accordance with conventional procedures by compressing mixtures of the active ingredients with a solid carrier and a lubricant. Examples of solid carriers include starch and sugar bentonite. Active ingredients can also be administered in a form of a hard shell tablet or a capsule containing a binder, e.g., lactose or mannitol, a conventional filler, and a tabletting agent. Pharmaceutical compositions can also be administered via the parenteral route. Examples of parenteral dosage forms include aqueous solutions, isotonic saline or 5% glucose of the active agent, or other well-known pharmaceutically acceptable excipients. Cyclodextrins, or other solubilising agents well-known to those familiar with the art, can be utilized as excipients for delivery of the therapeutic agent.

In certain embodiments, the composition of the invention comprises live *L. rhamnosus* HN001. Methods to produce such compositions are well-known in the art, and one such method is exemplified herein in the examples.

In other embodiments, the composition of the invention comprises one or more *L. rhamnosus* HN001 derivative. Again, methods to produce such compositions are well-known in the art, and may utilise standard microbiological and pharmaceutical practices.

It will be appreciated that a broad range of additives or carriers may be included in such compositions, for example to improve or preserve bacterial viability or to increase therapeutic efficacy of *L. rhamnosus* HN001 or of one or more *L. rhamnosus* HN001 derivatives. For example, additives such as surfactants, wetters, humectants, stickers, dispersal agents, stablisers, penetrants, and so-called stressing additives to improve bacterial cell vigor, growth, replication and survivability (such as potassium chloride, glycerol, sodium chloride and glucose), as well as cryoprotectants such as maltodextrin, may be included. Additives may also include compositions which assist in maintaining microorganism viability in long term storage, for example unrefined corn oil, or "invert" emulsions containing a mixture of oils and waxes on the outside and water, sodium alginate and bacteria on the inside.

In certain embodiments, the *L. rhamnosus* HN001 is in a reproductively viable form and amount.

The composition may comprise a carbohydrate source, such as a disaccharide including, for example, sucrose, fructose, glucose, or dextrose. Preferably the carbohydrate source is one able to be aerobically or anaerobically utilised by *L. rhamnosus* HN001.

In such embodiments, the composition preferably is capable of supporting reproductive viability of the *L. rhamnosus* HN001 for a period greater than about two weeks, preferably greater than about one month, about two months, about three months, about four months, about five months, more preferably greater than about six months, most preferably at least about 2 years to about 3 years or more.

In certain embodiments, an oral composition is formulated to allow the administration of a sufficient amount of *L. rhamnosus* HN001 to establish a population in the gastrointestinal tract of the subject when ingested. The established population may be a transient or permanent population.

In theory one colony forming unit (cfu) should be sufficient to establish a population of *L. rhamnosus* HN001 in a subject, but in actual situations a minimum number of units are required to do so. Therefore, for therapeutic mechanisms that are reliant on a viable, living population of probiotic bacteria, the number of units administered to a subject will affect therapeutic efficacy.

As presented herein in the examples, the Applicants have determined that a dosage rate of $6 \times 10^9$ cfu *L. rhamnosus* HN001 per day is sufficient (but may not be necessary) to establish a population in the gastrointestinal tract of human subjects. Accordingly, in one example, a composition formulated for administration will be sufficient to provide at least about $6 \times 10^9$ cfu *L. rhamnosus* HN001 per day.

Methods to determine the presence of a population of gut flora, such as *L. rhamnosus* HN001, in the gastrointestinal tract of a subject are well known in the art, and examples of such methods are presented herein. In certain embodiments, presence of a population of *L. rhamnosus* HN001 can be determined directly, for example by analysing one or more samples obtained from a subject, and determining the presence or amount of *L. rhamnosus* HN001 in said sample. In other embodiments, presence of a population of *L. rhamnosus* HN001 can be determined indirectly, for example by observing a reduction in eczema symptoms, or a decrease in the number of other gut flora in a sample obtained from a subject. Combinations of such methods are also envisaged.

The efficacy of a composition useful according to the invention can be evaluated both in vitro and in vivo. See, for example, the examples below. Briefly, the composition can be tested for its ability to prevent or treat eczema. For in viva studies, the composition can be fed to or injected into an animal model (e.g., a mouse) or administered to human subjects (including pregnant women) and its effects on incidence and severity of eczema and associated dermalogical conditions are then assessed. Based on the results, an appropriate dosage range and administration route can be determined.

Methods of calculating appropriate dose may depend on the nature of the active agent in the composition. For example, when the composition comprises live *L. rhamnosus* HN001, the dose may be calculated with reference to the number of live bacteria present. For example, as described herein the examples the dose may be established by reference to the number of colony forming units (cfu) to be administered per day. In examples where the composition comprises one or more *L. rhamnosus* HN001 derivatives, the dose may be calculated by reference to the amount or concentration of L. rhamnosus HN001 derivative present. For example, for a composition comprising L. rhamnosus HN001 cell lysate, the dose may be calculated by reference to the concentration of L. rhamnosus HN001 cell lysate present in the composition.

By way of general example, the administration of from about $1 \times 10^6$ cfu to about $1 \times 10^{12}$ cfu of L. rhamnosus HN001 per kg body weight per day, preferably about $1 \times 10^6$ cfu to about $1 \times 10^{11}$ cfu/kg/day, about $1 \times 10^6$ cfu to about $1 \times 10^{10}$ cfu/kg/day, about $1 \times 10^6$ cfu to about $1 \times 10^9$ cfu/kg/day, about $1 \times 10^6$ cfu to about $1 \times 10^8$ cfu/kg/day, about $1 \times 10^6$ cfu to about $5 \times 10^7$ cfu/kg/day, or about $1 \times 10^6$ cfu to about $1 \times 10^7$ cfu/kg/day, is contemplated. Preferably, the administration of from about $5 \times 10^6$ cfu to about $5 \times 10^8$ cfu per kg body weight of L. rhamnosus HN001 per day, preferably about $5 \times 10^6$ cfu to about $4 \times 10^8$ cfu/kg/day, about $5 \times 10^6$ cfu to about $3 \times 10^8$ cfu/kg/day, about $5 \times 10^6$ cfu to about $2 \times 10^8$ cfu/kg/day, about $5 \times 10^6$ cfu to about $1 \times 10^8$ cfu/kg/day, about $5 \times 10^6$ cfu to about $9 \times 10^7$ cfu/kg/day, about $5 \times 10^6$ cfu to about $8 \times 10^7$ cfu/kg/day, about $5 \times 10^6$ cfu to about $7 \times 10^7$ cfu/kg/day, about $5 \times 10^6$ cfu to about $6 \times 10^7$ cfu/kg/day, about $5 \times 10^6$ cfu to about $5 \times 10^7$ cfu/kg/day, about $5 \times 10^6$ cfu to about $4 \times 10^7$ cfu/kg/day, about $5 \times 10^6$ cfu to about $3 \times 10^7$ cfu/kg/day, about $5 \times 10^6$ cfu to about $2 \times 10^7$ cfu/kg/day, or about $5 \times 10^6$ cfu to about $1 \times 10^7$ cfu/kg/day, is contemplated.

In certain embodiments, periodic dose need not vary with body weight or other characteristics of the subject. In such examples, the administration of from about $1 \times 10^6$ cfu to about $1 \times 10^{13}$ cfu of L. rhamnosus HN001 per day, preferably about $1 \times 10^6$ cfu to about $1 \times 10^{12}$ cfu/day, about $1 \times 10^6$ cfu to about $1 \times 10^{11}$ cfu/day, about $1 \times 10^6$ cfu to about $1 \times 10^{10}$ cfu/day, about $1 \times 10^6$ cfu to about $1 \times 10^9$ cfu/day, about $1 \times 10^6$ cfu to about $1 \times 10^8$ cfu/day, about $1 \times 10^6$ cfu to about $5 \times 10^7$ cfu/day, or about $1 \times 10^6$ cfu to about $1 \times 10^7$ cfu/day, is contemplated. Preferably, the administration of from about $5 \times 10^7$ cfu to about $5 \times 10^{10}$ cfu per kg body weight of L. rhamnosus HN001 per day, preferably about $5 \times 10^7$ cfu to about $4 \times 10^{10}$ cfu/day, about $5 \times 10^7$ cfu to about $3 \times 10^{10}$ cfu/day, about $5 \times 10^7$ cfu to about $2 \times 10^{10}$ cfu/day, about $5 \times 10^7$ cfu to about $1 \times 10^{10}$ cfu/day, about $5 \times 10^7$ cfu to about $9 \times 10^9$ cfu/day, about $5 \times 10^7$ cfu to about $8 \times 10^9$ cfu/day, about $5 \times 10^7$ cfu to about $7 \times 10^9$ cfu/day, about $5 \times 10^7$ cfu to about $6 \times 10^9$ cfu/day, about $5 \times 10^7$ cfu to about $5 \times 10^9$ cfu/day, about $5 \times 10^7$ cfu to about $4 \times 10^9$ cfu/day, about $5 \times 10^7$ cfu to about $3 \times 10^9$ cfu/day, about $5 \times 10^7$ cfu to about $2 \times 10^9$ cfu/day, or about $5 \times 10^7$ cfu to about $1 \times 10^9$ cfu/day, is contemplated.

For example, as presented herein in the examples, an efficacious dose of freeze-dried L. rhamnosus HN001 was determined to be $6 \times 10^9$ cfu per day.

It will be appreciated that the composition is preferably formulated so as to allow the administration of an efficacious dose of L. rhamnosus HN001 or one or more derivatives thereof. The dose of the composition administered, the period of administration, and the general administration regime may differ between subjects depending on such variables as the severity of symptoms of a subject, the type of disorder to be treated, the mode of administration chosen, and the age, sex and/or general health of a subject. Furthermore, as described above the appropriate dose may depend on the nature of the active agent in the composition and the manner of formulation. For example, when the composition comprises live L. rhamnosus HN001, the dose may be calculated with reference to the number of live bacteria present. For example, as described herein the examples the dose may be established by reference to the number of colony forming units (cfu) to be administered per day. In examples where the composition comprises one or more L. rhamnosus HN001 derivatives, the dose may be calculated by reference to the amount or concentration of L. rhamnosus HN001 derivative to be administered per day. For example, for a composition comprising L. rhamnosus HN001 cell lysate, the dose may be calculated by reference to the concentration of L. rhamnosus HN001 cell lysate present in the composition.

It will be appreciated that preferred compositions are formulated to provide an efficacious dose in a convenient form and amount. In certain embodiments, such as but not limited to those where periodic dose need not vary with body weight or other characteristics of the subject, the composition may formulated for unit dosage. It should be appreciated that administration may include a single daily dose or administration of a number of discrete divided doses as may be appropriate. For example, as presented herein in the examples, an efficacious dose of L. rhamnosus HN001 may be formulated into a capsule for oral administration.

However, by way of general example, the inventors contemplate administration of from about 1 mg to about 1000 mg per kg body weight of a composition useful herein per day, preferably about 50 to about 500 mg per kg per day, alternatively about 150 to about 410 mg/kg/day or about 110 to about 310 mg/kg/day. In one embodiment, the inventors contemplate administration of from about 0.05 mg to about 250 mg per kg body weight of a composition useful herein.

Examples of infant formula, follow-on formula, or growing-up formula are presented herein. Compositions such as these may be formulated so that the concentration of L. rhamnosus HN001 present in the composition is such that an efficacious dose can be prepared using a readily measurable amount of the composition. For example, in certain embodiments, such as for example where the composition is an infant formula, the L. rhamnosus HN001 is provided at a concentration sufficient to supply an efficacious dose in an amount of formula capable of being easily measured by a parent or caregiver when preparing the formula for administration, such as, for example, with a measured scoop or similar as are commonly provided with infant formulas. Exemplary non limiting concentrations of L. rhamnosus HN001 for use in such compositions include from about $5 \times 10^5$ cfu per gram of formula to about $10^9$ cfu per gram of formula, or from about $10^6$ cfu per gram of formula to about $10^8$ cfu per grain of formula.

In one embodiment a composition useful herein comprises, consists essentially of, or consists of at least about 0.1, 0.2, 0.5, 1, 5, 10, 15, 20, 25, 30, 35, 40, 45, 50, 55, 60, 65, 70, 75, 80, 85, 90, 95, 99, 99.5, 99.8 or 99.9% by weight of L. rhamnosus HN001 or a derivative thereof and useful ranges may be selected between any of these foregoing values (for example, from about 0.1 to about 50%, from about 0.2 to about 50%, from about 0.5 to about 50%, from about 1 to about 50%, from about 5 to about 50%, from about 10 to about 50%, from about 15 to about 50%, from about 20 to about 50%, from about 25 to about 50%, from about 30 to about 50%, from about 35 to about 50%, from about 40 to about 50%, from about 45 to about 50%, from about 0.1 to about 60%, from about 0.2 to about 60%, from about 0.5 to about 60%, from about 1 to about 60%, from about 5 to about 60%, from about 10 to about 60%, from about 15 to about 60%, from about 20 to about 60%, from about 25 to about 60%, from about 30 to about 60%, from about 35 to about 60%, from about 40 to about 60%, from about 45 to about 60%, from about 0.1 to about 70%, from about 0.2 to about 70%, from about 0.5 to about 70%, from about 1 to about 70%, from about 5 to about 70%, from about 10 to about 70%, from about 15 to about 70%, from about 20 to about 70%, from about 25 to about 70%, from about 30 to about 70%, from about 35 to about 70%, from about 40 to about 70%, from about 45 to about 70%, from about 0.1 to about 80%, from about 0.2 to about 80%, from about 0.5 to about 80%, from about 1 to about 80%, from about 5 to about 80%, from about 10 to about 80%, from about 15 to about 80%, from about 20 to about 80%, from about 25 to about 80%, from about 30 to about 80%, from about 35 to about 80%, from about 40 to about 80%, from about 45 to about 80%, from about 0.1 to about 90%, from about 0.2 to about 90%, from about 0.5 to about 90%, from about 1 to about 90%, from about 5 to about 90%, from about 10 to about 90%, from about 15 to about 90%, from about 20 to about 90%, from about 25 to about 90%, from about 30 to about 90%, from about 35 to about 90%, from about 40 to about 90%, from about 45 to about 90%, from about 0.1 to about 99%, from about 0.2 to about 99%, from about 0.5 to about 99%, from about 1 to about 99%, from about 5 to about 99%, from about 10 to about 99%, from about 15 to about 99%, from about 20 to about 99%, from about 25 to about 99%, from about 30 to about 99%, from about 35 to about 99%, from about 40 to about 99%, and from about 45 to about 99%).

In one embodiment a composition useful herein comprises, consists essentially of, or consists of at least about 0.001, 0.01, 0.05, 0.1, 0.15, 0.2, 0.3, 0.4, 0.5, 1, 2, 3, 4, 5, 6, 7, 8, 9, 10, 11, 12, 13, 14, 15, 16, 17, 18 or 19 grams of L. rhamnosus HN001 or a derivative thereof and useful ranges may be selected between any of these foregoing values (for example, from about 0.01 to about 1 grams, about 0.01 to about 10 grams, about 0.01 to about 19 grams, from about 0.1 to about 1 grams, about 0.1 to about 10 grams, about 0.1 to about 19 grams, from about 1 to about 5 grams, about 1 to about 10 grams, about 1 to about 19 grams, about 5 to about 10 grams, and about 5 to about 19 grams).

In one embodiment a composition useful herein comprising L. rhamnosus HN001 or a derivative thereof additionally comprises about 0.1, 0.5, 1, 5, 10, 15, 20, 25, 30, 35, 40, 45, 50, 55, 60, 65, 70, 75, 80, 85, 90, 95, 97, 99, or 99.9% by weight of fresh whole milk or a milk derivative and useful ranges may be selected between any of these foregoing values (for example, from about 0.1 to about 50%, from about 0.2 to about 50%, from about 0.5 to about 50%, from about 1 to about 50%, from about 5, to about 50%, from about 10 to about 50%, from about 15 to about 50%, from about 20 to about 50%, from about 25 to about 50%, from about 30 to about 50%, from about 35 to about 50%, from about 40 to about 50%, and from about 45 to about 50%). The milk derivative is preferably selected from recombined, powdered or fresh skim milk, recombined or reconstituted whole or skim milk powder, skim milk concentrate, skim milk retentate, concentrated milk, ultrafiltered milk retentate, milk protein concentrate (MPC), milk protein isolate (MPI), calcium depleted milk protein concentrate (MPC), low fat milk, low fat milk protein concentrate (MPC), casein, caseinate, milk fat, cream, butter, ghee, anhydrous milk fat (AMF), buttermilk, butter serum, beta serum, hard milk fat fractions, soft milk fat fractions, sphingolipid fractions, milk fat globular membrane fractions, milk fat globular membrane lipid fractions, phospholipid fractions, complex lipid fractions, colostrum, a colostrum fraction, colostrum protein concentrate (CPC), colostrum whey, an immunoglobulin fraction from colostrum, whey (including sweet whey, lactic acid whey, mineral acid whey, or reconstituted whey powder), whey protein isolate (WPI), whey protein concentrate (WPC), a composition derived from any milk or colostrum processing stream, a composition derived from the retentate or permeate obtained by ultrafiltration or microfiltration of any milk or colostrum processing stream, a composition derived from the breakthrough or adsorbed fraction obtained by chromatographic (including but not limited to ion and gel permeation chromatography) separation of any milk or colostrum processing stream, extracts of any of these milk derivatives including extracts prepared by multistage fractionation, differential crystallisation, solvent fractionation, supercritical fractionation, near critical fractionation, distillation, centrifugal fractionation, or fractionation with a modifier (e.g. soaps or emulsifiers), hydrolysates of any of these derivatives, fractions of the hydrolysates, and any combination of any two or more of these derivatives, including combinations of hydrolysed and/or non-hydrolysed fractions. It should be understood that the source of these derivatives may be milk or colostrum or a combination thereof.

It will be apparent that the concentration of L. rhamnosus HN001 or one or more derivatives thereof in a composition formulated for administration may be less than that in a composition formulated for, for example, distribution or storage, and that the concentration of a composition formulated for storage and subsequent formulation into a composition suitable for administration must be adequate to allow said composition for administration to also be sufficiently concentrated so as to be able to be administered at a therapeutically efficacious dose.

The compositions useful herein may be used alone or in combination with one or more other therapeutic agents. The therapeutic agent may be a food, drink, food additive, drink additive, food component, drink component, dietary supplement, nutritional product, medical food, nutraceutical, medicament or pharmaceutical. The therapeutic agent may be a probiotic agent or a probiotic factor, and is preferably effective to treat, prevent or attenuate eczema or one or more of the symptoms of eczema.

When used in combination with another therapeutic agent, the administration of a composition useful herein and the other therapeutic agent may be simultaneous or sequential. Simultaneous administration includes the administration of a single dosage form that comprises all components or the administration of separate dosage forms at substantially the same time. Sequential administration includes administration according to different schedules, preferably so that there is an overlap in the periods during which the composition useful herein and other therapeutic agent are provided.

Suitable agents with which the compositions useful herein can be separately, simultaneously or sequentially administered include one or more probiotic agents, one or more prebiotic agents, one or more phospholipids, one or more gangliosides, other suitable agents known in the art, and combinations thereof. Useful prebiotics include galactooligosaccharides (GOS), short chain GOS, long chain GOS, fructooligosaccharides (FOS), short chain FOS, long chain FOS, inulin, galactans, fructans, lactulose, and any mixture of any two or more thereof. Some prebiotics are reviewed by Boehm G and Moro G (Structural and Functional Aspects of Prebiotics Used in Infant Nutrition, J. Nutr. (2008) 138(9): 1818S-1828S), incorporated herein by reference. Other useful agents may include dietary fibre such as a fully or partially insoluble or indigestible dietary fibre. Accordingly, in one embodiment L. rhamnosus HN001 or derivative thereof may be administered separately, simultaneously or sequentially with one or more agents selected from one or more probioitics, one or more prebiotics, one or more sources of dietary fibre, one or more galactooligosaccharides, one or more short chain galactooligosaccharides, one or more long chain galactooligosaccharides, one or more fructooligosaccharides, one or more short chain galactooligosaccharides, one or more long chain galactooligosaccharides, inulin, one or more galactans, one or more fructans, lactulose, or any mixture of any two or more thereof.

In one embodiment, a composition useful herein includes or is administered simultaneously or sequentially with milk components such as whey protein, whey protein fractions (including acidic or basic whey protein fractions or a combination thereof), glycomacropeptide, lactoferrin, iron-lactoferrin, a functional lactoferrin variant, a functional lactoferrin fragment, a vitamin D or calcium, or combinations thereof. Useful milk component-containing compositions include compositions such as a food, drink, food additive, drink additive, dietary supplement, nutritional product, medical food or nutraceutical. Milk fractions enriched for these components may also be employed. Useful lactoferrins, fragments and compositions are described in international patent applications WO 03/082921 and WO 2007/043900, both incorporated herein by reference in their entirety.

It should be understood that the additional therapeutic agents listed above (both food based and pharmaceutical agents) may also be employed in a method according to the invention where they are administered separately, simultaneously or sequentially with a composition useful herein.

In one embodiment a composition useful herein further comprises a pharmaceutically acceptable carrier. In another embodiment the composition is or is formulated as a food, drink, food additive, drink additive, dietary supplement, nutritional product, medical food, enteral feeding product, parenteral feeding product, meal replacement, cosmeceutical, nutraceutical, medicament, or pharmaceutical. In one embodiment the composition is in the form of a tablet, a caplet, a pill, a hard or soft capsule or a lozenge. In one embodiment the composition is in the form of a cachet, a powder, a dispensable powder, granules, a suspension, an elixir, a liquid, or any other form that can be added to food or drink, including for example water, milk or fruit juice. In one embodiment the composition further comprises one or more constituents (such as antioxidants) which prevent or reduce degradation of the composition during storage or after administration. These compositions may include any edible consumer product which is able to carry bacteria or bacterial derivatives, including heat-killed, pressure-killed, lysed, UV- or light-treated, irradiated, fractionated or otherwise killed or attenuated bacteria. Examples of suitable edible consumer products include aqueous products, baked goods, confectionary products including chocolate, gels, ice creams, reconstituted fruit products, snack bars, food bars, muesli bars, spreads, sauces, dips, dairy products including yoghurts and cheeses, drinks including dairy and non-dairy based drinks, milk, milk powders, sports supplements including dairy and non-dairy based sports supplements, fruit juice, food additives such as protein sprinkles, dietary supplement products including daily supplement tablets, weaning foods and yoghurts, and formulas such as infant formula, follow-on formula, or growing-up formula, in powder or liquid form. Suitable nutraceutical compositions useful herein may be provided in similar forms.

It will be appreciated that different compositions of the invention may be formulated with a view to administration to a particular subject group. For example, the formulation of a composition suitable to be administered to a pregnant mother (for example, for indirect administration to a foetal subject or to a breastfeeding neonatal, infant, or child subject) may differ to that of a composition to be directly administered to the subject. It should also be appreciated that the formulation of a composition to be administered prophylactically may differ to that of a composition formulated for administration once eczema or one or more symptoms of eczema is present.

In one embodiment the composition for prophylactic use may further comprise or the *L. rhamnosus* HN001 may be used in combination with a probiotic agent such as *Lactobacillus rhamnosus* GG, *Lactobacillus acidophilus* (for example, *Lactobacillus acidophilus* (LAVRI-A1), *Lactobacillus reuteri* (for example *Lactobacillus reuteri* ATCC 55730) or *Bifidobacteria lactis* (for example, *Bifidobacteria lactis* strain HN019) or a combination of any two or more thereof.

In one embodiment, compositions for prophylactic administration, and particularly prophylactic indirect administration, may further comprise or the *L. rhamnosus* HN001 may be used in combination with a probiotic agent such as *Lactobacillus rhamnosus* GG, *Lactobacillus acidophilus* (for example, *Lactobacillus acidophilus* (LAVRI-A1), *Lactobacillus reuteri* (for example *Lactobacillus reuteri* ATCC 55730) or *Bifidobacteria lactis* (for example, *Bifidobacteria lactis* strain HN019) or a combination of any two or more thereof.

It will be appreciated that the term "prophylactic" and grammatical equivalents as used herein contemplates treatment, use, administration and the like before eczema or the symptoms of eczema are apparent.

In embodiments for use in the treatment of a subject having eczema or one or more symptoms of eczema, the composition may further comprise or the *L. rhamnosus* HN001 may be combination with a probiotic agent such as *Lactobacillus rhamnosus* GG, *Lactobacillus acidophilus* (for example, *Lactobacillus acidophilus* (LAVRI-A1), *Lactobacillus reuteri* (for example *Lactobacillus reuteri* ATCC 55730) or *Bifidobacteria lactis* (for example, *Bifidobacteria lactis* strain HN019) or a combination of any two or more thereof, with the proviso that such compositions for direct administration to an infant or child subject of one year or more in age having eczema or one or more symptoms of eczema do not comprise *Bifidobacteria lactis* strain HN019.

As used herein, the term "therapeutic" and grammatical equivalents contemplate treatment, uses or administration where eczema or the symptoms of eczema are present.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

3 Eczema

Eczema is generally considered to be a form of dermatitis, and is believe to result from inflammation of the epidermis and the inability of the skin to retain moisture. Eczema is frequently used interchangeably with dermatitis, and somewhat confusingly, some view dermatitis as a form of eczema. Eczema may be thought of as a broad term used to describe a set of clinical characteristics. Reported causes of eczema include lifestyle habits, dietary habits, temperature, allergies, medication, exposure to chemicals, and hereditary predisposition.

There are many types of eczema, the most common being:

Atopic eczema: This is the most common form of eczema, and is also known as infantile eczema, flexural eczema or atopic dermatitis. Atopic eczema is believed to be hereditary, as it often runs in families whose members also have allergic reactions such as asthma and hay fever. This form of eczema is particularly noticeable on head and scalp, neck, inside of elbows, behind knees, and buttocks. This form of eczema is often confused with contact dermatitis.

Contact dermatitis: There are two types of contact dermatitis: (1) Allergic (due to the presence of an allergen such as poison ivy), and (2) Irritant (due to direct contact with a solvent). Some substances are both allergens and irritants (wet cement, for example). Some substance cause phototoxic dermatitis when exposed to sunlight. Contact eczema can be treated by removing and avoiding the allergen or irritant.

Xerotic eczema: Xerotic eczema is also known as asteatotic eczema, and occurs when the skin is very dry. The limbs and the trunk of the body are most affected where the affected areas are dry and cracked. This form of eczema is common amongst the elderly. It has been suggested that xerotic eczema and ichthyosis are related conditions.

Seborrhoeric dermatitis: This type of eczema is better known as dandruff. It is characterized by dry or greasy scaling of the scalp and the eyebrows. Occurrence in infants has been proposed to be a result of a lack of biotin.

Other: There are many other less common eczemas such as dyshidrosis, discoid eczema, venous eczema, Duhring's disease, neurodermatitis, autoeczematization and others. There are also eczemas caused by underlying diseases, infection or ingestion of medications, foods or chemicals.

3.1 Symptoms:

The symptoms of eczema include dryness and recurring skin rashes characterised by redness, skin edema, itching, crusting of the skin, flaking, blistering, cracking, oozing, or bleeding. It will be appreciated that the severity of these symptoms can vary widely. After healing there is normally a slight skin discoloration but there is rarely scarring. Dryness and rashes are normally found on the flexor part of the joints.

3.2 Diagnosis:

Unsurprisingly given the above, a wide variety of criteria have been proposed for the diagnosis of eczema. However, recognition of standardised criteria for the diagnosis of eczema and for establishing the severity of eczema is becoming more widespread. See, for example, Williams H C, Burney P G J, Hay R J, Archer C B, Shipley M J, Hunter J J A, et al. The UK Working Party's Diagnostic Criteria for Atopic Dermatitis. Br J Dermatol 1994; 131:383-96; Williams H. 'So How Do I Define Atopic Eczema? A Practical Manual for Researchers Wanting to Define Atopic Eczema' 1996, http://www.nottingham.ac.uk/dermatology/eczema/contents/html; and European Task Force on Atopic Dermatitis. Severity Scoring of Atopic Dermatitis: the SCORAD Index. Dermatology 1993; 186:23-31.

3.3 Current Treatments:

As there is no known cure for eczema, current treatment regimes are directed to suppressing symptoms. Current treatments utilise:

Corticosteroids: Corticosteroid creams or lotions are highly effective but have side-effects such as thinning of skin, HPA axis suppression, skin infections and glaucoma if applied to the eye. Generally weak corticosteroids will be used on less severe cases such as hydrocortisone, whereas moderate to severe cases will require higher-potency steroids such as triancinolone and fluocinonide. In some cases, oral or IV corticosteroids may be used, but typically only for acute treatments.

Immunomodulators: Immunomodulators suppress the immune system in the affected area and have been reported as more effective that corticosteroids in certain populations. Side effects include severe flushing, photosensitive reactivity and possible interactions with even small amounts of consumed alcohol. There are conflicting'reports on the association of immunomodulators with increased risk of cancer.

Immunosuppressants: Immunosuppressants are typically reserved for use in patients with severe eczema that is not responsive to other eczema treatments. They work by reducing a subject's immune system and result in highly effective results in severe cases, but have numerous side effects. Common immunosuppressants used in the treatment of eczema include cyclosporine, azathioprine and methotrexate.

Anti-itch drugs: Anti-itch drugs, such as anti-histamines, naloxone, capsaicin and menthol, can be used to reduce itching sensations and as a result to provide some kind of relief to eczema suffurors. Moisturizers are also used to sooth the skin in order to reduce the pain and urge to itch, while increasing moisture content to combat dryness.

Light therapy: Ultraviolet light can help control eczema. There is, however, the associated risk of skin cancer. Normally UVA and UVB wavelengths are used. Photo-chemotherapy, such as PUVA (psoralen and UVA), is also used.

Antibiotics: While not a direct treatment for eczema, antibiotics are frequently prescribed to stop opportunistic infections, for example, when the skin surface is broken due to excess scratching or dryness.

Topical calcineurin inhibitors: These inhibitors reduce inflammation and have been effective in the treatment of eczema. Side-effects include risk of cancer and risk of infections. Treatment with calcineurin inhibitors, such as pimecrolimus and tacrolimus, is discouraged in people who have a weakened immune system.

3.4 Eczema in Pregnancy:

There is little or no evidence to suggest that eczema impacts on pregnancy. However, pregnancy is associated with increased occurrence or severity of eczema in some sufferers. Treatment options during pregnancy are limited, where pregnant mothers are advised to use only. UVB, mild to potent steroids, or emollients. The use of very potent topical steroids, oral steroids, cyclosporine, methotrexate, azathioprine, PUVA, and topical calcineurin inhibitors is strongly discouraged during pregnancy.

Various aspects of the invention will now be illustrated in non-limiting ways by reference to the following examples.

EXAMPLE

To determine whether probiotic supplementation in early life could prevent development of eczema and atopy at two years, a double-blind, randomized placebo-controlled trial of infants at risk of allergic disease was conducted.

Materials and Methods

Pregnant women in Auckland and Wellington, New Zealand, were recruited to the study through maternity care providers, antenatal classes, and advertisements. They were invited to take part in the study if they or the infant's father had a history of treated asthma, eczema, or hay fever. Women were ineligible for the study if they planned to move from the study center in the next 2 years, were already taking probiotic supplements long-term, or intended to use these in the child. They were not able to continue in the study if they delivered before 37 weeks gestation, they had not taken the study capsules for ≥2 weeks before birth, their infant's weight was <3rd percentile for sex and gestation, or their infant was placed in the neonatal unit for more than 48 hours or had serious congenital abnormalities at birth. If there were twins, only the heavier was included in the study.

Study Design

The study was a two-centre, double-blind, randomized, placebo-controlled trial of the effects of probiotic supplementation on the development of eczema and atopic sensitization in infants (Australian New Zealand Clinical Trials Registry: ACTRN12607000518460). There were two treatment groups who received either *L. rhamnosus* HN001 ($6 \times 10^9$ colony-forming units/day) or *B. animalis* subsp *lactis* HN019 ($9 \times 10^9$ colony-forming units/day) (Fonterra Co-Operative Group, Auckland, New Zealand).

The probiotic supplements were manufactured by using aseptic fermentation, concentration, and freeze-drying. The growth media contained skim milk powder, yeast extract, and glucose. After growth, cells of the HN001 and HN019 strains were concentrated by centrifugation and washed twice with sterile saline. During prototype development of the low-allergenic probiotic supplements, the separate ingredients were tested by skin prick test (SPT) on several patients with cow's milk allergy. This work established that after two washes, the material had no reaction in the patients with cow's milk allergy. The final washed cells were mixed with a cryoprotectant solution, maltodextrin and this mix was frozen on trays and freeze-dried. The resulting powder had a particle size of 200 microns or less and was tested for the presence of pathogens before dispatch to a registered pharmaceutical packaging company. The placebo group received a capsule identical in appearance and smell containing dextran, salt, and a yeast extract (Fonterra Co-operative Group). The yeast extract used in the probiotics and the placebo contained no viable cells.

All batches of capsules were tested monthly to ensure viability of the probiotics. Shelf life was managed to ensure minimum cell counts were maintained. In addition, capsules returned from the field were tested for their viability. With very few exceptions, the viability was higher than the minimum required.

At 35 weeks gestation, pregnant women were randomized to receive one of the probiotics or placebo daily, to continue while they were breast-feeding for as long as 6 months postpartum. Infants started the capsules between 2 and 16 days postbirth (median=6 days), continuing until age 2 years. The capsule powder was either given undiluted to the infant or mixed with water, breast milk, or formula and given via a teaspoon or syringe until solid food was started, when it was sprinkled on food.

Randomization and allocation of supplements were performed by a clinical trials pharmacist at Auckland City Hospital who had no contact with the participants. Randomization was stratified by study center and performed in blocks of 15 according to a computer-generated randomization list. At enrollment, a research study nurse assigned the next study number and provided the participant with the appropriate capsules. All study nurses and participants were blind to treatment assignment for the duration of the study. To evaluate the efficacy of the blinding, the final questionnaire asked participants to indicate whether they believed they were in a probiotic or placebo group.

Information collected at baseline included parental history of allergic disease; sex; ethnicity; household smoking; pet exposure; and length, weight, and head circumference at birth. Eczema prevalence and severity were assessed at follow-up visits at 3, 6, 12, and 18 months and 2 years, and SPTs performed at 2 years to assess atopic sensitization. History of antibiotic use was also collected at these visits.

Ethical approval was granted by a national multi-region ethics committee, covering both study centers.

Outcome Measures

Eczema prevalence from birth to 2 years was defined using the UK Working Party's Diagnostic Criteria for atopic dermatitis (Williams H C, Burney P G J, Hay R J, Archer C B, Shipley M J, Hunter J J A, et al. The UK Working Party's Diagnostic Criteria for Atopic Dermatitis. British Journal of Dermatology. 1994; 131:383-96) modified for use in infants. Eczema was determined to be present at each visit if there was a history of scratching or rubbing and two or more of the following occurring since birth or the previous visit: (1) a history of involvement of outer arms or legs, (2) a history of a generally dry skin, or (3) visible atopic eczema present on the cheeks or outer arms or legs with no axillary involvement. The research staff were trained in determining eczema by using an internationally recognized training manual for defining atopic eczema (Williams H. 'So How Do I Define Atopic Eczema? A Practical Manual for Researchers Wanting to Define Atopic Eczema' 1996, http://www.nottingham.ac.uk).

Eczema severity from birth to 2 years was assessed by using SCORing Atopic Dermatitis (SCORAD) (European Task Force on Atopic Dermatitis. Severity Scording of Atopic Dermatitis: the SCORAD Index. Dermatology 1993; 186:23-31) in all children regardless of their eczema diagnosis (as defined). SCORAD was analyzed dichotomously using a cutoff ≥10 to exclude those with trivial rash. All staff were trained to apply SCORAD in a standardized way.

After training in the use of a standardized protocol, (ASCIA Skin Prick Testing Working Party. Skin prick testing for the diagnosis of allergic disease: a manual for practitioners. 2006. Available at: http://www.allergy.org.au/images/stories/pospapers/ASCIA_SPT_Manual_Sep_06.pdf), the study nurse performed SPTs at 2 years to egg white, peanut, cow's milk, cat pelt, *Dermatophagoides pteronyssinus*, and mixed grass pollen (Hollister-Stier, Spokane, Wash.). This panel of allergens has been shown to identify 90% of atopic children at 15 months who were tested to a wider range of allergens (Epton M, Town I, Ingham T, Wickens K, Fishwick D; Crane J, et al. The New Zealand Asthma and Allergy Cohort Study (NZA2CS): assembly, demographics and investigations. BMC Public Health 2007; 7:26). Antihistamine medication was withheld for an appropriate period. The allergens and positive (histamine 10 mg/mL) and negative control were applied to the child's arm and pricked vertically for 1 second using Dome-Hollister-Stier lancets (United Kingdom). The histamine response was read at 10 minutes, and allergens and negative control at 15 minutes. A 3 mm or greater mean wheal diameter to 1 or more allergens after subtraction of the negative control wheal diameter and with a positive response to histamine was considered positive. For safety reasons, 6 children who had previously had a severe allergic reaction to a food and a positive SPT response for that food were not retested for the food but considered positive on the basis of the previous test. IgE-associated eczema was defined as eczema plus a positive SPT response, and non-IgE-associated eczema as eczema plus a negative SPT response.

Fecal Sample Collection

Fecal samples were collected from infants soon after birth and at 3, 12, and 24 months of age. The samples were held in the home freezer until transportation to the research center for storage at −80° C. Bacterial DNA was extracted from feces by using a previously described method (Tannock G, Munro K, Harmsen H, Welling G, Smart J, Gopal P. Analysis of the fecal microflora of human subjects consuming a probiotic containing *Lactobacillus rhamnosus* DR20. Appl Environ Microbiol 2000; 66:2578-88). Bifidobacterial DNA was amplified by using PCR primers targeting the transaldolase gene, (Requena T, Burton J, Matsuki T, Munro K, Simon M, Tanaka R, et al. Identification, detection, and enumeration of human *Bifidobacterium* species by PCR targeting the transaldolase gene. Appl Environ Microbiol 2002; 68:2420-7) and *Lactobacillus* amplicons were obtained by using PCR primers targeting the 16S ribosomal RNA gene (Walter J, Hertel C, Tannock G, Lis C, Munro K, Hammes W. Detection of *Lactobacillus, Pediococcus, Leuconostic* and *Weisella*II species in human feces by using group-specific PCR primers and denaturing gradient gel electrophoresis. Appl Environ Microbiol 2001; 67:2578-85). Denaturing gradient gel electrophoresis was performed by using a Bio-Rad DCode universal mutation detection system (Bio-Rad, Hercules, Calif). Gradient concentrations and electrophoretic conditions have been described previously (Requena T, Burton J, Matsuki T, Munro K, Simon M, Tanaka R, et al. Identification, detection, and enumeration of human Bifidobacterium species by PCR targeting the transaldolase gene. Appl Environ Microbiol 2002; 68:2420-7; Walter J, Hertel C, Tannock G, Lis C, Munro K, Hammes W. Detection of *Lactobacillus, Pediococcus, Leuconostic* and *Weisella*II species in human feces by using group-specific PCR primers and denaturing gradient gel electrophoresis. Appl Environ Microbiol 2001; 67:2578-85.). PCR amplicons generated from DNA extracted from pure cultures of *B. animalis* subsp *lactis* HN019 and *L. rhamnosus* HN001 were used as markers in relation to fecal profiles in gels. Visual comparisons of fecal profiles with strain markers thus permitted the detection of *B. animalis* subsp *lactis* and *L. rhamnosus* in the fecal samples. Detection was at the species level because strain-specific PCR primers were not available.

Compliance

Bottles of capsules were replaced every 3 months and counted by a member of staff who had no participant involvement.

Sample Size

Sample size calculation was based on a 50% cumulative prevalence of eczema by 2 years in the control group. To detect an 18% absolute reduction in eczema caused by probiotics, with 80% power at the 5% significance level, 127 were needed in each study group. To allow for a 25% loss because of ineligibility at birth or subsequent withdrawal, 170 mothers were enrolled in each group.

Statistical Analysis

Analysis was undertaken by using SAS version 9.0 (SAS Institute, Cary, N.C.). Differences between study groups in the cumulative prevalence of eczema or SCORAD (≥10) at each age were summarized by using Kaplan-Meier curves and proportional hazard models. Proportional hazard models were also used to assess differences in study groups in the point prevalence of atopy, and variables dependent on atopy, at 2 years. The persistence of *L. rhamnosus* and *B. animalis* subsp *lactis* in fecal samples over the study period was defined as detection of these bacteria on 2 or more occasions versus detection on 1 occasion only or absence of detection to limit the effect of adventitious exposure from food and other environmental sources. Odds ratios were used to assess associations between the persistence of each bacterium in feces and the 2-year prevalence of eczema and SCORAD ≥10, and the point prevalence of atopic sensitization at 2 years. The presence or absence of each probiotic species in fecal samples was also analyzed by study group at each time point. All children who completed the study were included in an intention-to treat analysis regardless of their compliance. The chi-square test was used to compare differences between groups and differences at baseline, with P<0.05 considered statistically significant. Because baseline differences were small, these variables were not adjusted for in the analysis of the outcome variables.

Compliance was calculated as the number of capsules taken as a proportion of the number of days in the study period.

Results

Participants were recruited from January 2004 to May 2005 at an average rate of 7 per week. Among randomized participants who received treatment, 87.7%, 84.7%, and 88.9% in the placebo, *L. rhamnosus* HN001, and *B. animalis* subsp *lactis* HN019 groups, respectively, completed the study (see FIG. 1). Among participants who were eligible at birth, 94.3%, 91.7%, and 96.2% in the placebo, *L. rhamnosus* HN001, and *B. animalis* subsp *lactis* HN019 groups, respectively, completed the study (see FIG. 1). Of these, there were 6 participants in the placebo group, 17 in the *L. rhamnosus* HN001 group, and 12 in the *B. animalis* subsp *lactis* HN019 group who discontinued treatment but who continued to be followed up until the end of the study. One mother in the placebo group and 3 mothers in the *B. animalis* subsp *lactis* HN019 group gave their reasons for discontinuing treatment as a result of perceived side effects of, or opposition to, taking study capsules. All these participants provided outcome data at each time point and were included in an intention-to-treat analysis. An additional 9, 13, and 6 in the placebo, *L. rhamnosus* HN001, and *B. animalis* subsp *lactis* HN019 groups, respectively, withdrew from the study completely and could not be included in an intention-to-treat analysis. None of these withdrawals was a result of perceived side effects of study treatment.

There were no significant differences between the groups in the proportion of participants who took more than 75% of the study capsules. Defined this way, the compliance rates were 77.3%, 73.6%, and 78.3%, in the placebo, *L. rhamnosus* HN001, and *B. animalis* subsp *lactis* HN019 groups, respectively.

There were no significant differences between study groups in baseline characteristics (see Table I below).

TABLE I

Prevalence of study characteristics of eligible children in the placebo (n = 159), *L. rhamnosus* HN001 (n = 157) and *B. lactis* HN019 (n = 158) groups.

|  | Placebo n (%) | *L. rhamnosus* HN001 n (%) | *B. lactis* HN019 n (%) | P value* |
|---|---|---|---|---|
| Female | 76 (47.8) | 79 (50.3) | 73 (46.2) | 0.76 |
| Ethnicity |  |  |  |  |
| Maori | 18 (11.5) (*157*) | 15 (9.6) (*157*) | 15 (9.6) (*156*) | 0.83 |
| European | 121 (77.1) (*157*) | 129 (82.2) (*157*) | 124 (79.5) (*156*) |  |
| Other | 18 (11.5) (*157*) | 13 (8.3) (*157*) | 17 (10.9) (*156*) |  |
| Birth |  |  |  |  |
| Caesarean | 50 (31.5) | 46 (29.3) | 57 (36.1) | 0.42 |
| Mean (SD) birth weight (kg) | 3.48 (0.4) (*157*) | 3.48 (0.4) (*157*) | 3.47 (0.5) (*156*) | 1.00 |
| Mean (SD) birth length (cm) | 51.5 (2.0) (*156*) | 51.7 (1.9) (*157*) | 51.5 (2.0) (*156*) | 0.63 |
| Mean (SD) head circumference cm) | 35.4 (1.3) (*157*) | 35.6 (1.2) (*157*) | 35.5 (1.3) (*156*) | 0.55 |
| Breastfeeding |  |  |  |  |
| Breastfeeding ever | 152 (95.6) | 153 (97.5) | 154 (97.5) | 0.55 |
| Mean duration (SD) (months) | 9.9 (5.7) (*147*) | 9.8 (5.5) (*143*) | 9.6 (6.1) (*151*) | 0.89 |
| Environmental exposures |  |  |  |  |
| Smoking in pregnancy | 4 (2.5) | 5 (3.2) | 7 (4.4) | 0.57 |
| Any smoking inside or outside | 19 (12.0) | 25 (15.9) | 18 (11.4) | 0.61 |
| Any pet | 77 (48.4) | 70 (44.6) | 83 (52.5) | 0.37 |
| Family history |  |  |  |  |
| Family history of eczema** | 119 (74.8) | 114 (72.6) | 119 (75.3) | 0.84 |
| Maternal history of allergic disease*** | 134 (84.3) | 132 (84.1) | 133 (84.2) | 1.00 |
| Paternal history of allergic disease*** | 104 (65.4) | 111 (70.7) | 107 (67.7) | 0.60 |
| Antibiotic use during study | 129 (86.0) | 118 (81.9) | 129 (84.9) | 0.35 |

Figure 2:
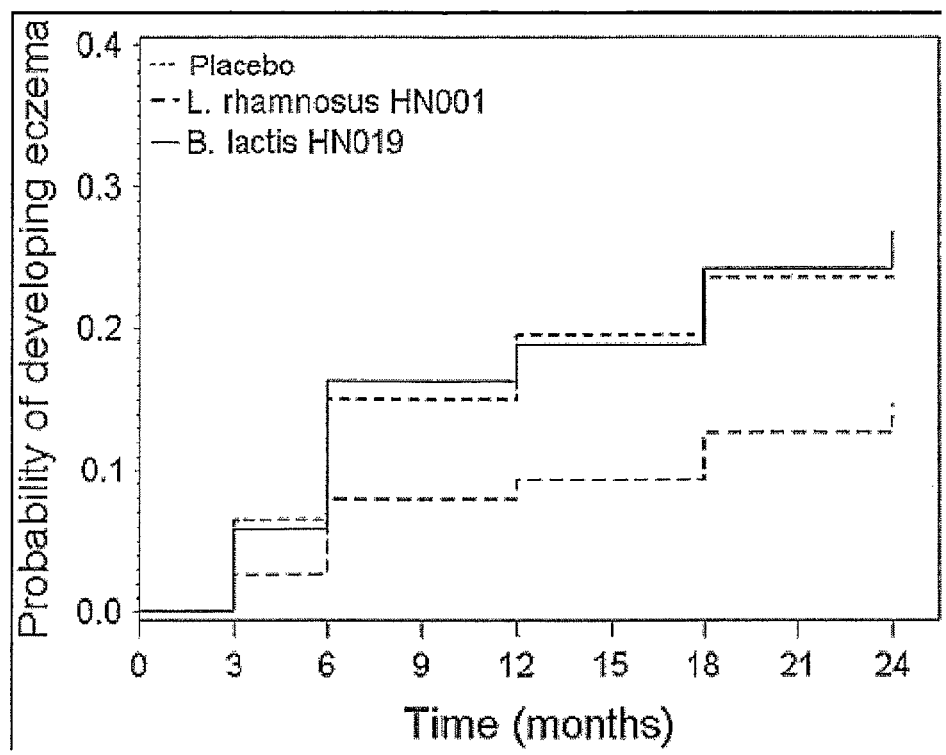
FIG. 2 is a Kaplan-Meier plot showing the 2-year cumulative prevalence of eczema in infants taking placebo, *L. rhamnosus* HN001, or *B. animalis* subsp *lactis* HN019.
Figure 3:
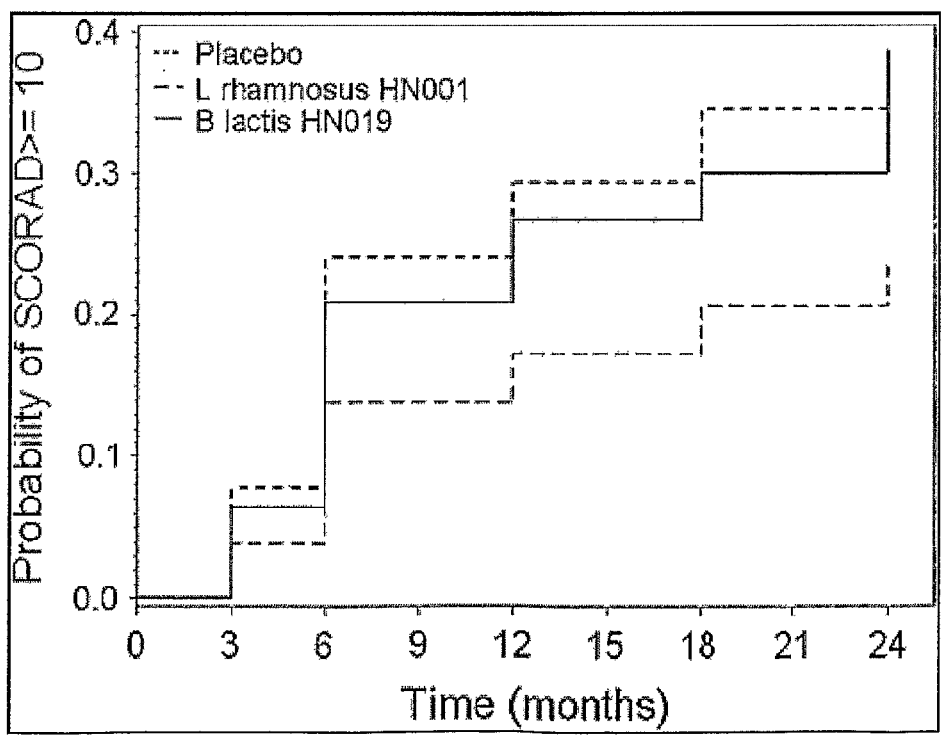
FIG. 3 is a Kaplan-Meier plot showing the 2-year cumulative prevalence of SCORAD ≥10 in infants taking placebo, *L. rhamnosus* HN001, or *B. animalis* subsp *lactis* HN019.

Sample sizes are shown in italics if different from those shown in the heading
*p value chi sq test for difference between the 3 study groups
**restricted to those treated by a doctor
***defined as asthma, eczema or hayfever with at least one disease treated by a doctor Infants receiving *L. rhamnosus* HN001 had a significantly reduced risk of developing eczema by 2 years (14.8%) compared with infants in the placebo group (26.8%; Table II; FIG. 2). The number needed to treat was 8.3. The hazard ratio was similar for those with IgE-associated eczema and those whose eczema was not IgE-associated, although not statistically significant in the latter group (see Table II below). There was no statistically significant effect of either probiotic on the likelihood of having a positive skin test result for any allergen, or for food allergens, at 2 years (Table II). The risk of developing SCORAD ≥10 was significantly reduced by 2 years in the *L. rhamnosus* HN001 group (Table II; FIG. 3). In contrast, there was no effect of *B. animalis* subsp *lactis* HN019 on eczema prevalence or SCORAD ≥10 by 2 years (Table II; FIGS. 2 and 3).

TABLE II

Hazard ratios (95% CIs) for the 2 year cumulative prevalence of eczema and SCORAD ≥ 10, and point prevalence of atopy in infants taking *L. rhamnosus* HN001 and *B. lactis* HN019.

|  | Placebo N = 159 | *L. rhamnosus* HN001 N = 157 | P value | *B. lactis* HN019 N = 158 | P value | P value* |
|---|---|---|---|---|---|---|
| Eczema | 1.00 (26.8%) | 0.51 (0.30-0.85) (14.8%) | 0.01 | 0.90 (0.58-1.41) (24.2%) | 0.64 | 0.03 |
| SCORAD ≥ 10 | 1.00 (38.7%) | 0.57 (0.38-0.87) (24.0%) | 0.009 | 0.99 (0.69-1.43) (37.3%) | 0.97 | 0.02 |
| Eczema prevalence + SCORAD ≥ 10 | 1.00 (22.9%) | 0.52 (0.30-0.91) (12.8%) | 0.02 | 0.98 (0.61-1.57) (22.2%) | 0.93 | 0.047 |
|  | N = 146 | N = 141 |  | N = 149 |  |  |
| Atopy to any allergen | 1.00 (28.8%) | 0.74 (0.46-1.18) (21.3%) | 0.21 | 0.82 (0.52-1.28) (23.5%) | 0.38 | 0.42 |
| Atopy to food allergens | 1.00 (21.2%) | 0.74 (0.43-1.27) (15.6%) | 0.22 | 0.70 (0.40-1.20) (14.8%) | 0.19 | 0.35 |
| IgE-associated eczema | 1.00 (18.5%) | 0.51 (0.27-0.97) (9.9%) | 0.04 | 0.69 (0.38-1.24) (12.8%) | 0.21 | 0.11 |

TABLE II-continued

Hazard ratios (95% CIs) for the 2 year cumulative prevalence of eczema and SCORAD ≥ 10, and point prevalence of atopy in infants taking *L. rhamnosus* HN001 and *B. lactis* HN019.

| Non-IgE-associated eczema | 1.00 (8.9%) | 0.52 (0.21-1.30) (5.0%) | 0.16 | 1.28 (0.62-2.63) (11.4%) | 0.57 | 0.13 |

*p value chi square test for difference between the 3 study groups

Fifty-eight infants were exposed to commercially available nonstudy probiotics short-term either directly or through the mother's breast milk during the course of the study. After excluding these infants, the associations with eczema prevalence by 2 years for *L. rhamnosus* HN001 (hazard ratio [HR], 0.45; 95% CI, 0.26-0.78; P 0.004) and *B. animalis* subsp *lactis* HN019 (HR, 0.87; 95% CI, 0.56-1.38; P 0.56) strengthened slightly.

Figure 4:
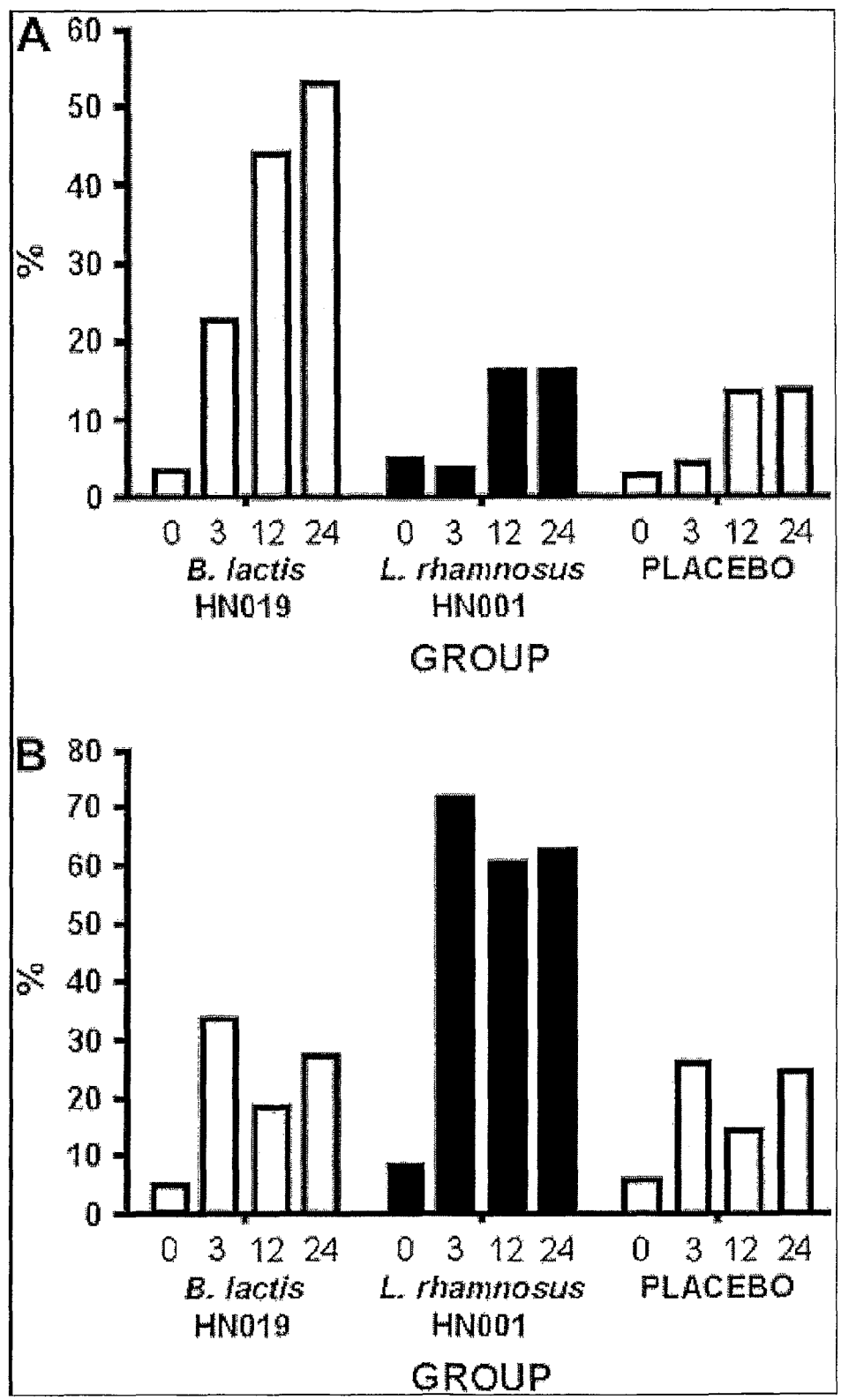
FIG. 4 is two graphs showing (A) the percentage of subjects in which *B. animalis* subsp *lactis* was detected at each time point (in months) for each infant group (administered *B. animalis* subsp *lactis* HN019, *L. rhamnosus* HN001, or placebo); and (B) the percentage of subjects in which *L. rhamnosus* was detected at each time point (in months) for each infant group (administered *B. animalis* subsp *lactis* HN019, *L. rhamnosus* HN001, or placebo).

*B. animalis* subsp *lactis* and *L. rhamnosus* were detected in the feces of infants in the placebo and alternative probiotic group at birth, pointing to the adventitious inoculation of the alimentary tract with these bacteria from environmental sources (Ahrne S, Nobeck S, Jeppson B, Adlerberth I, Wold A, Molin G. The normal *Lactobacillus* flora of healthy human rectal and oral mucosa. J Appl Microbiol 1998; 85:88-94; Janet C, Arigoni F, Lee B, Pelaez C, Requena T. Enzymatic ability of *Bifidobacterium animalis* subsp. *lactis* to hydrolyze milk proteins: identification and characterization to endopeptidase O. Appl Environ Microbiol 2005; 71: 8460-5; Kim S-Y, Adachi Y. Biological and genetic classification of canine intestinal lactic acid bacteria and bifidobacteria. Microbiol Immunol 2007; 51:919-28; Mah K, Chin V, Wong W, Lay C, Tannock G, Shek L, et al. Effect of milk formula containing probiotics on the fecal microbiota of Asian infants at risk of atopic diseases. Pediatr Res 2007; 62:674-9.) (FIG. 4, A and B). However, administration of a probiotic resulted in markedly increased detection rates for that probiotic in fecal samples at 3, 12, and 24 months compared with the other groups (P<0.0001). Detection of *B. animalis* subsp *lactis* in fecal samples increased progressively over the course of the study from 22.6% at 3 months to 53.1% at 24 months among infants administered HN019 (FIG. 4, A). In contrast, detection of *L. rhamnosus* was greatest at 3 months at 71.5% and was slightly lower at 24 months at 62.3% among infants administered this probiotic (FIG. 4B).

There was no relationship between the persistence (2 or more samples positive) of *B. animalis* subsp *lactis* in feces and the development of eczema (odds ratio [OR], 1.21; 95% CI, 0.63-2.33; P 0.58), atopic sensitization (OR, 1.01; 95% CI, 0.52-1.94; P 0.98), or eczema severity (OR, 1.04; 95% CI, 0.57-1.88; P 0.90) by 2 years. There was a trend toward a lower prevalence of eczema (OR, 0.65; 95% CI, 0.38-1.11; P 0.12) and atopic sensitization (OR, 0.73; 95% CI, 0.44-1.21; P 0.22) that reached significance for SCORAD ≥10 (OR, 0.56; 95% CI, 0.35-0.90; P 0.02) among infants with persistent *L. rhamnosus* in feces.

At the end of the study, parents were asked whether they thought they were in a probiotic or placebo group. More than half the respondents in each study group could not offer an opinion, 14.7% of the placebo group participants thought they had received a placebo, and 23.7% of the *B. animalis* subsp *lactis* HN019 group and 25.7% of the *L. rhamnosus* HN001 group thought they were in a probiotic group.

Discussion

In this study, treatment with *L. rhamnosus* HN001 for the first 2 years of life was associated with a reduction in the prevalence of any eczema by about a half. Treatment with *L. rhamnosus* HN001 also showed a strong protective effect against having a SCORAD value ≥10.

Despite some disparities between studies, the weight of evidence suggests a protective role for some *Lactobacillus* species in the pathogenesis of eczema, but there is little evidence overall that this is mediated through effects on allergic sensitization. The suggestion of Kukkonen et al (Kukkonen K, Savilahti E, Haahtela T, Juntunen-Backman K, Korpela R, Poussa T, et al. Probiotics and prebiotics galacto-oligosaccharides in the prevention of allergic disease: a randomized, double-blind, placebo-controlled trial. J Allergy Clin Immunol 2007; 119:192-8) that probiotics regulate the pathway from sensitization to clinical disease is not supported by the findings presented herein, which show the effect of *L. rhamnosus* HN001 is similar for sensitized and non-sensitized eczema.

A number of immunologic pathways have been proposed to be affected by probiotics, involving several different mechanisms. For example, it has been suggested that probiotic influences may be local, and potentially include reduction of permeability and systemic penetration of antigens; alteration of local inflammation or tolerance induction; anti-inflammatory effects mediated by Toll-like receptors; activation of tolerogenic dendritic cells; TH1 skewing of responses; alteration of T-regulatory function; and increased local IgA production. Systemic effects with increased monocytes and effects on T cells, B cells, and stem cells have also been suggested (Prescott S, Bjorksten B. Probiotics for the prevention or treatment of allergic diseases. J Allergy Clin Immunol. 2007; 120:255-62). Some strains of lactobacilli and bifidobacteria have been shown to modulate IL-10 production, thereby, it has been suggested, enhancing regulatory or tolerance-inducing mechanisms (Niers L, Timmerman H, Rijkers G, van Bleek G, van Uden N, Knol E, et al. Identification of strong interleukin-10 inducing lactic acid bacteria which down-regulate T helper type 2 cytokines. Clin Exp Allergy 2005; 35:1481-9).

In this study, cord blood IFN-gamma levels were higher and more often detectable among the probiotic groups, but this was statistically significant only for the *L. rhamnosus* HN001 group (Prescott S L, Wicken K, Westcott L, Nieblee J, Currie H, Black P, et al. Supplementation with *Lactobacillus rhamnosus* or *Bifidobacterium lactis* probiotics in pregnancy increases cord blood IFN-gamma and breast milk TGF-beta and IgA detection. Clin Exp Allergy 2008. In press).

The presence of bifidobacteria and lactobacilli in the feces of participants was investigated because it has rarely been established whether probiotic cultures can pass through the infant gastrointestinal tract and reach the colon when administered in trials of long duration (Mah K, Chin V, Wong W, Lay C, Tannock G, Shek L, et al. Effect of milk formula containing probiotics on the fecal microbiota of Asian infants at risk of atopic diseases. Pediatr Res 2007; 62:674-9). Different distributions in the detection rate of each probiotic between birth and 24 months were observed.

Without wishing to be bound by any theory, this might be a result of the changing ecosystem within the infant bowel as the characteristic shifts in bacterial community composition occur over time (Mali K, Chin V, Wong W, Lay C, Tannock G, Slick L, et al. Effect of milk formula containing probiotics on the fecal microbiota of Asian infants at risk of atopic diseases. Pediatr Res 2007; 62:674-9). *B. animalis* subsp *lactis* was detected at relatively low frequency during the first 3 months of administration. *L. rhamnosus* detection in the feces was boosted by HN001 administration, but even so, after subtraction of background exposure to this species, less than half of the infants had detectable DNA from this species in their feces. A recent report from Singapore (Mah K, Chin V, Wong W, Lay C, Tannock G, Shek L, et al. Effect of milk formula containing probiotics on the fecal microbiota of Asian infants at risk of atopic diseases. Pediatr Res 2007; 62:674-9) showed that peak detection (after subtraction of background exposure) of a *Bifidobacterium longum* strain in infant feces occurred at 3 days after intervention commenced (44% of infants), falling to 26% and 16% after 1 and 3 months, respectively, of probiotic administration. In that study (Mah K, Chin V, Wong W, Lay C, Tannock G, Shek L, et al. Effect of milk formula containing probiotics on the fecal microbiota of Asian infants at risk of atopic diseases. Pediatr Res 2007; 62:674-9) detection of *L. rhamnosus* GG was 83% after 3 days of administration, then' 77% and 69%, respectively, after 1 and 3 months of administration. Analytical methods of detection of fecal bacteria based on bulk-extracted DNA do not provide information about viability of the bacteria in the bowel with DNA potentially derived from active, quiescent, or dead bacterial cells. Nevertheless, the bacteriologic results of this study are notable because they reveal the relative abilities of the bifidobacteria and lactobacilli to transit the gastrointestinal tract.

There has been controversy about whether probiotics prevent the development of eczema. This study provides evidence that *L. rhamnosus* HN001 is an effective intervention for reducing the prevalence of eczema among high-risk children. This comparison of 2 different probiotics demonstrates that not all probiotics are equally effective in the treatment or prophylaxis of a particular condition or in obtaining any particular treatment outcome.

INDUSTRIAL APPLICABILITY

This invention relates to the use of probiotic bacteria, particularly *Lactobacillus rhamnosus* HN001 or derivatives thereof, and in particular in the treatment or prevention of eczema. Methods for using the bacteria and compositions comprising the bacteria are also provided.

What we claim is:

1. A method of treating or preventing eczema in a subject, the method comprising oral administration of an effective amount of the viable *Lactobacillus rhamnosus* HN001, AGAL deposit number NM97/09514 dated 18 Aug. 1997, to a subject in need thereof.

2. The method of claim 1, wherein the viable *Lactobacillus rhamnosus* HN001 is administered in a composition comprising a physiologically acceptable diluent, adjuvant, carrier or excipient.

3. The method of claim 2, wherein the composition comprises an infant formula, a follow-on formula, a growing-up formula, a maternal formula, a maternal supplement, a dietetic product, or a food.

4. The method of claim 3, wherein the food comprises cultured milk, yoghurt, cheese, milk drink or milk powder.

5. The method of claim 2, wherein the composition is a pharmaceutical composition and the excipient or diluent comprises a pharmaceutically acceptable diluent, adjuvant, carrier or excipient.

6. The method of claim 1 wherein the method is a method of preventing eczema.

7. The method of claim 1 wherein the subject is a neonatal, an infant, or a child subject.

8. The method of claim 1, wherein if the subject is a juvenile or an adult subject, the method comprises administering a composition comprising the viable *Lactobacillus rhamnosus* HN001 to the subject.

9. The method of claim 1, wherein the *Lactobacillus rhamnosus* HN001 is in a reproductively viable form.

10. The method of claim 1, wherein the eczema is atopic eczema.

11. The method of claim 1, wherein the viable *Lactobacillus rhamnosus* HN001 is administered separately, simultaneously or sequentially with one or more agents selected from one or more probioitics, one or more prebiotics, one or more sources of dietary fibre, one or more galactooligosaccharides, one or more short chain galactooligosaccharides, one or more long chain galactooligosaccharides, one or more fructooligosaccharides, one or more short chain galactooligosaccharides, one or more long chain galactooligosaccharides, inulin, one or more galactans, one or more fructans, lactulose, or any mixture of any two or more thereof.

12. The method of claim 1 wherein from about $5 \times 10^7$ cfu to about $1 \times 10^{10}$ cfu per day of *Lactobacillus rhamnosus* HN001 is administered.

13. The method of claim 1 wherein the effective amount of *Lactobacillus rhamnosus* HN001 is about $6 \times 10^9$ cfu per day.

14. A method of treating or preventing eczema in a foetal subject or in a breastfeeding neonatal, breastfeeding infant or breastfeeding child subject, the method comprising oral administration of an effective amount of the viable *Lactobacillus rhamnosus* HN001, AGAL deposit number NM97/09514 dated 18 Aug. 1997 to the individual pregnant with the foetal subject, or the individual breastfeeding the breastfeeding neonatal, breastfeeding infant or breastfeeding child subject in need thereof.

15. The method of claim 14, wherein the viable *Lactobacillus rhamnosus* HN001 is administered in a composition comprising a physiologically acceptable diluent, adjuvant, carrier or excipient.

* * * * *

UNITED STATES PATENT AND TRADEMARK OFFICE
CERTIFICATE OF CORRECTION

PATENT NO. : 9,737,575 B2
APPLICATION NO. : 13/130522
DATED : August 22, 2017
INVENTOR(S) : Julian Crane It is certified that error appears in the above-identified patent and that said Letters Patent is hereby corrected as shown below:

On the Title Page

In Column 1 (page 2, item (56)) at Line 25, Under Other Publications, before "120," insert --vol.--.

In Column 2 (page 2, item (56)) at Line 38, Under Other Publications, change "HNO01" to --HN001--.

In Column 2 (page 2, item (56)) at Line 40, Under Other Publications, change "Allergey," to --Allergy,--.

In the Specification

In Column 1 at Line 39, Change "LAVR1-A1," to --LAVRI-A1,--.

In Column 2 at Line 2, Change "ore" to --more--.

In Column 2 at Line 62, Change "seborrhoeric" to --seborrhoeic--.

In Column 5 at Line 24, Change "Genebank" to --Genbank--.

In Column 9 at Line 58, Change "stablisers," to --stabilisers,--.

In Column 10 at Line 50, Change "viva" to --vivo--.

In Column 10 at Lines 54-55, Change "dermalogical" to --dermatological--.

In Column 12 at Line 45, Change "grain" to --gram--.

In Column 15 at Line 1, Change "probioitics," to --probiotics,--.

Signed and Sealed this
Twenty-seventh Day of February, 2018

Andrei Iancu
*Director of the United States Patent and Trademark Office*

CERTIFICATE OF CORRECTION (continued)
U.S. Pat. No. 9,737,575 B2

In Column 17 at Line 27, Change "Seborrhoeric" to --Seborrhoeic--.

In Column 18 at Line 3, Change "triancinolone" to --triamcinolone--.

In Column 18 at Line 11, Change "conflicting'reports" to --conflicting reports--.

In Column 18 at Line 24, Change "suffurors." to --sufferers.--.

In Column 18 at Line 46, Change "only." to --only--.

In Column 25 at Line 26, Change "Janet" to --Janer--.

In Column 25 at Line 36, Change "(FIG." to --(FIGS.--.

In Column 25 at Line 43, Change "(FIG." to --(FIGS.--.

In Column 27 at Line 5, Change "Slick L," to --Shek L,--.

In Column 27 at Line 26, Change "then'" to --then--.

In the Claims

In Column 27 at Line 56, In Claim 1, change "1997," to --1997--.

In Column 28 at Line 30, In Claim 11, change "probioitics," to --probiotics,--.